(12) United States Patent
Zhu et al.

(10) Patent No.: US 11,513,094 B2
(45) Date of Patent: Nov. 29, 2022

(54) ELECTROCHEMICAL DETECTION ELECTRODE AND MANUFACTURING METHOD THEREOF, ELECTROCHEMICAL DETECTION APPARATUS

(71) Applicant: BOE TECHNOLOGY GROUP CO., LTD., Beijing (CN)

(72) Inventors: Lin Zhu, Beijing (CN); Xinguo Li, Beijing (CN); Wenbo Li, Beijing (CN)

(73) Assignee: BEIJING BOE TECHNOLOGY DEVELOPMENT CO., LTD., Beijing (CN)

( * ) Notice: Subject to any disclaimer, the term of this patent is extended or adjusted under 35 U.S.C. 154(b) by 370 days.

(21) Appl. No.: 16/621,351

(22) PCT Filed: Jun. 19, 2019

(86) PCT No.: PCT/CN2019/091871
§ 371 (c)(1),
(2) Date: Dec. 11, 2019

(87) PCT Pub. No.: WO2020/073679
PCT Pub. Date: Apr. 16, 2020

(65) Prior Publication Data
US 2021/0333230 A1 Oct. 28, 2021

(30) Foreign Application Priority Data
Oct. 11, 2018 (CN) .......................... 201811184740.X

(51) Int. Cl.
*G01N 27/327* (2006.01)
*G01N 27/30* (2006.01)
*G01N 33/483* (2006.01)

(52) U.S. Cl.
CPC ........ *G01N 27/301* (2013.01); *G01N 27/302* (2013.01); *G01N 27/3272* (2013.01); *G01N 27/3278* (2013.01); *G01N 33/4836* (2013.01)

(58) Field of Classification Search
CPC .... G01N 27/327–3272; G01N 27/3275–3278; G01N 27/30;
(Continued)

(56) References Cited

U.S. PATENT DOCUMENTS

2013/0306485 A1* 11/2013 Varghese ........... G01N 33/6815
205/171
2021/0333230 A1* 10/2021 Zhu ..................... G01N 27/3278

FOREIGN PATENT DOCUMENTS

CN 101430300 A 5/2009
CN 102901754 A 1/2013
(Continued)

OTHER PUBLICATIONS

Tungkavet et al., "Improvements of electromechanical properties of gelatin hydrogels by blending with nanowire polypyrrole: effects of electric field and temperature," Polym Int 2012; 61: 825-833 (Year: 2012).*

(Continued)

*Primary Examiner* — Alexander S Noguerola
(74) *Attorney, Agent, or Firm* — Syncoda LLC; Feng Ma

(57) ABSTRACT

An electrochemical detection electrode includes: a plurality of electrode structures; and a plurality of groups of detection structures on the plurality of electrode structures; wherein: the plurality of groups of detection structures include a first group of detection structures and a second group of detection structures, each of the first group of detection structures on one of the plurality of electrode structures having a first shape in a plane parallel to a surface of one of the plurality of electrode structures is configured to combine with a first (Continued)

detection object, each of the second group of detection structures on one of the plurality of electrode structures having a second shape in a plane parallel to a surface of one of the plurality of electrode structures is configured to combine with a second detection object; and wherein the first shape is different from the second shape.

16 Claims, 16 Drawing Sheets

(58) Field of Classification Search
CPC .. G01N 33/4836; G01N 27/02; G01N 27/021; G01N 27/04
See application file for complete search history.

(56) References Cited

FOREIGN PATENT DOCUMENTS

| CN | 104303056 A | 1/2015 |
| CN | 104593840 A | 5/2015 |

OTHER PUBLICATIONS

CN first Office Action in Application No. 201811184740.X, dated Aug. 1, 2019.

* cited by examiner

ELECTROCHEMICAL DETECTION ELECTRODE AND MANUFACTURING METHOD THEREOF, ELECTROCHEMICAL DETECTION APPARATUS

CROSS-REFERENCE TO RELATED APPLICATION

The present application claims priority to Chinese Patent Application No. 201811184740.X filed on Oct. 11, 2018, the disclosure of which is hereby incorporated by reference in its entirety.

TECHNICAL FIELD

The present disclosure relates to an electrochemical detection electrode and manufacturing method thereof and an electrochemical detection apparatus.

BACKGROUND

Electrochemistry is a part of physical chemistry, disciplines related to electrochemistry include inorganic chemistry, analytical chemistry, organic chemistry and so on, electrochemistry also relates to fields such as metal industry, environmental sciences, energy sciences, imaging, electronics, biology and medical sciences. Electrochemical detection is a convenient detection method based on electrochemical principles, it has the advantages such high sensitivity, low power consumption, ease of implementation with automatically controls, and low cost. It has been applied widely in a variety of fields such as environmental monitoring and electrochemical analysis.

SUMMARY

In a first aspect, an electrochemical detection electrode is provided, including:
a plurality of electrode structures; and
a plurality of groups of detection structures on the plurality of electrode structures;
wherein:
the plurality of groups of detection structures comprise a first group of detection structures and a second group of detection structures, each of the first group of detection structures on one of the plurality of electrode structures having a first shape in a plane parallel to a surface of one of the plurality of electrode structures is configured to combine with a first detection object, each of the second group of detection structures on one of the plurality of electrode structures having a second shape in a plane parallel to a surface of one of the plurality of electrode structures is configured to combine with a second detection object; and
wherein the first shape is different from the second shape.

In some embodiments, the plurality of groups of detection structures are a plurality of detection grooves integrated on the plurality of electrode structures.

In some embodiments, the plurality of electrode structures have a material of gelatin configured to be deformed in response to an electric current applied thereto.

In some embodiments, each of the plurality of groups of detection structures comprises a material of temperature memory or a material of pH sensitivity.

In some embodiments, the first group of detection structures comprise a material of first temperature memory, each of the first group of detection structures has a first shape in the plane parallel to the surface of one of the plurality of electrode structures in a first temperature, the second group of detection structures are a material of second temperature memory, each of the second group of detection structures has a second shape in the plane parallel to the surface of one of the plurality of electrode structures in a second temperature.

In some embodiments, the plurality of electrode structures comprises a first group of electrode structures and a second group of electrode structures, all of the first group of detection structures are on the first group of electrode structures, all of the second group of detection structures are on the second group of electrode structures.

In some embodiments, each of the plurality of electrode structures comprises a first part and a second part, some of the first group of detection structures are on the first part, some of the second group of detection structures are on the second part.

In some embodiments, some of the first group of detection structures on the first part are a material of graphene film layer, some of the second group of detection structures on the second part are a material of a diamond film layer.

In some embodiments, each of the plurality of electrode structures further includes a third part, the plurality of groups of detection structures further comprises a third group of detection structures, some of the third group of detection structures on the third part are a material of diamond-like carbon film layer.

In some embodiments, the electrochemical detection electrode further includes a plurality of connection structures electrically connected to the plurality of electrode structures, wherein the plurality of connection structures are configured to transmit electric signals to the plurality of electrode structures and receive electric signals output by the plurality of electrode structures.

In some embodiments, the plurality of connection structures and the plurality of electrode structures are in one-to-one correspondence.

In some embodiments, the plurality of detection grooves have a shape of a triangle, a diamond, a rectangle, or a circle.

In some embodiments, the electrochemical detection electrode further includes:
a plurality of detection regions, wherein multiple groups of detection grooves of different shapes are respectively located in different detection regions.

In some embodiments:
the plurality of detection regions comprises a first detection region, a second detection region, and a third detection region;
a surface of the electrode structure in the first detection region is covered by a graphene film layer;
a surface of the electrode structure in the second detection region is covered by a diamond-like carbon film layer; and
a surface of the electrode structure in the third detection region is covered by a diamond film layer.

In some embodiments:
the second detection region includes a plurality of detection sub-regions; and
characteristics of the diamond-like carbon film in at least two detection sub-region are different.

In some embodiments:
the electrode structure comprises a plurality of sub-structures; and
the detection grooves are formed over the surfaces of the sub-structures.

In some embodiments, the plurality of sub-structures are provided in a form of an array or in a form of a stack structure.

In some embodiments, the plurality of sub-structures have a shape of a cube, a cuboid, or a cylinder.

In some embodiments, the sub-structures are three-dimensional cavities.

In another aspect, an electrochemical detection apparatus is provided, including:

the electrochemical detection electrode; and multiple groups of detection carriers;

wherein the multiple groups of detection carriers are configured so as to be respectively utilized for surface adsorption of substances to be detected and combined with the multiple groups of detection structures of different shapes of the electrochemical detection electrode during a detection process.

In some embodiments, shapes of cross-sections of the detection carriers include triangles, diamonds, rectangles, or circles.

In some embodiments, the electrochemical detection apparatus further includes a detection circuit, wherein:

the detection circuit is electrically coupled to the electrochemical detection electrode;

the detection circuit is configured to transmit electric signals to the electrochemical detection electrode and receive electric signals output by the electrochemical detection electrode.

In some embodiments, the electrochemical detection apparatus further includes a working condition controller configured to control working conditions of the electrochemical detection electrode.

In some embodiments, the working condition controller is configured to control at least one of temperature, PH value, or electric field strength.

In some embodiments, a method of manufacturing the electrochemical detection electrode is provided, the method including:

forming an electrode structure over a substrate; and forming detection grooves over the electrode structure.

In some embodiments, the forming the electrode structure and the forming the detection grooves comprise at least one of a microelectronic lithography process, a 3D/4D printing process, a mechanical machining process, a laser processing, a physical self-assembly process, or a chemical self-assembly process.

In some embodiments, the forming the electrode structure and the forming the detection grooves comprise forming a plurality of micron-scale detection structures with the physical self-assembly process.

In some embodiments, the forming the electrode structure and the forming the detection grooves comprise forming a plurality of nano-scale structures with the chemical self-assembly process.

In another aspect, a method of detecting characteristics of a material with the electrochemical detection electrode is provided, the method including determining characteristics or presence of the material based on at least one of an electrical current through the electrochemical detection electrode or a resistance change of the electrochemical detection electrode.

In some embodiments, the method further includes determining a quantity of the material based on an amplitude of the electrical current or the resistance change.

In some embodiments, the method further includes controlling working conditions of the electrochemical detection electrode to thereby detect characteristics of different materials.

In some embodiments, the working conditions include at least one of a temperature or a pH value.

In some embodiments, the working conditions comprise a temperature, the method further comprising varying the temperature to thereby control a shape of microstructures of the electrode to thereby combine with different molecules.

The chemical detection electrode of present disclosure can realize respectively detecting different substances, with a high detection efficiency, sensitivity, and uniformity, with a wide detection range.

BRIEF DESCRIPTION OF DRAWINGS

To more clearly illustrate some of the embodiments, the following is a brief description of the drawings.

The drawings in the following descriptions are only illustrative of some embodiments. For those of ordinary skill in the art, other drawings of other embodiments can become apparent based on these drawings.

DETAILED DESCRIPTION

Figure 1:
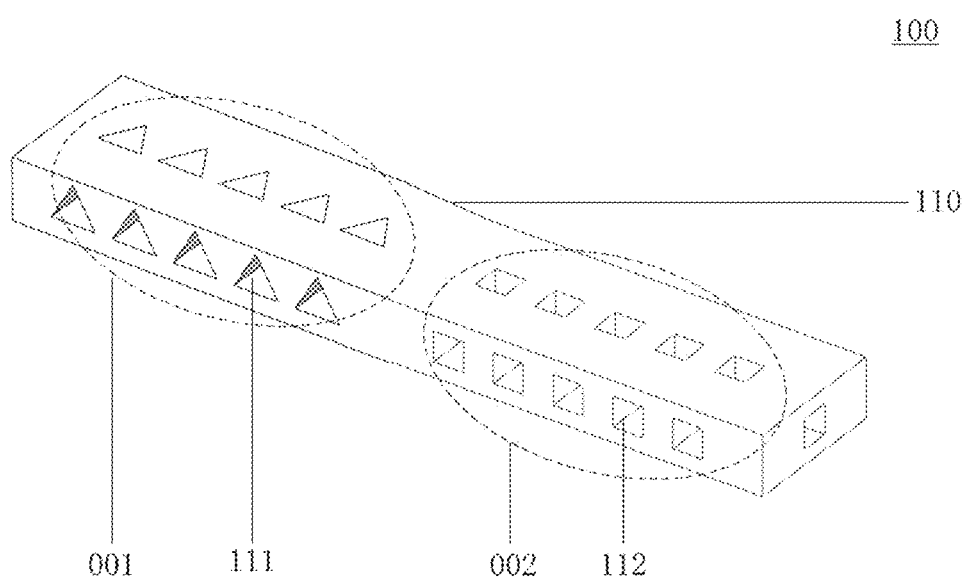
FIG. 1 illustrates an exemplary perspective view of an electrochemical detection electrode according to some embodiments of the present disclosure.

The embodiments set forth below represent the necessary information to enable those skilled in the art to practice the embodiments and illustrate the best mode of practicing the embodiments. Upon reading the following description in light of the accompanying drawing figures, those skilled in the art will understand the concepts of the disclosure and will recognize applications of these concepts not particularly addressed herein. It should be understood that these concepts and applications fall within the scope of the disclosure and the accompanying claims.

It will be understood that, although the terms first, second, etc. can be used herein to describe various elements, these elements should not be limited by these terms. These terms are only used to distinguish one element from another. For example, a first element could be termed a second element, and, similarly, a second element could be termed a first element, without departing from the scope of the present disclosure. As used herein, the term "and/or" includes any and all combinations of one or more of the associated listed items.

It will be understood that when an element such as a layer, region, or other structure is referred to as being "on" or extending "onto" another element, it can be directly on or extend directly onto the other element or intervening elements can also be present. In contrast, when an element is referred to as being "directly on" or extending "directly onto" another element, there are no intervening elements present.

Likewise, it will be understood that when an element such as a layer, region, or substrate is referred to as being "over" or extending "over" another element, it can be directly over or extend directly over the other element or intervening elements can also be present. In contrast, when an element is referred to as being "directly over" or extending "directly over" another element, there are no intervening elements present. It will also be understood that when an element is referred to as being "connected" or "coupled" to another element, it can be directly connected or coupled to the other element or intervening elements can be present. In contrast, when an element is referred to as being "directly connected" or "directly coupled" to another element, there are no intervening elements present.

Relative terms such as "below" or "above" or "upper" or "lower" or "horizontal" or "horizontal" can be used herein to describe a relationship of one element, layer, or region to another element, layer, or region as illustrated in the drawings. It will be understood that these terms and those discussed above are intended to encompass different orientations of the device in addition to the orientation depicted in the Figures.

The terminology used herein is for the purpose of describing particular embodiments only and is not intended to be limiting of the disclosure. As used herein, the singular forms "a," "an," and "the" are intended to include the plural forms as well, unless the context clearly indicates otherwise. It will be further understood that the terms "comprises," "comprising," "includes," and/or "including" when used herein specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this disclosure belongs. It will be further understood that terms used herein should be interpreted as having a meaning that is consistent with their meaning in the context of this specification and the relevant art and will not be interpreted in an idealized or overly formal sense unless expressly so defined herein.

Various embodiments of the present disclosure provide an electrochemical detection electrode and manufacturing method thereof a chemical detection device can be provided, the chemical detection electrode can include an electrode structure, the electrode structure can include multiple groups of detection grooves of different shapes, the multiple groups of detection grooves of different shapes can be provided such that they can be combined with detection objects of different shapes. The chemical detection electrode of present disclosure can realize the function of respectively detecting different substances, the detection efficiency is high, the detection sensitivity is high, uniformity is good and applicable range is wide.

In the field of electrochemical detection, electrochemical electrode can usually be utilized to conduct detection. For example, an electrochemical detection electrode can include a working electrode, a reference electrode and a counter electrode.

Usually, a gold electrode or a glassy carbon electrode can be utilized as a working electrode, a silver electrode or a silver chloride electrode can be utilized as a reference electrode, a platinum wire/plate can be utilized as a counter electrode. The electrodes can be simultaneously inserted in a container that contains reaction solution. For example, the electrodes can be connected to a control unit provided in a separate row. The control unit, for example, can include a circuit and/or a processor.

Oxidoreduction reaction can happen to the substance to be detected in the reaction solution over the surface of the working electrode and a certain electric signal can be generated (for example, an electrical current), a control unit can be utilized to detect and process the electric current, thus the detection of the substance to be detected can be realized.

With the development of technologies, electrochemical detection electrodes become smaller and smaller. The working electrode in an electrochemical detection electrode can be a gold electrode or a glassy carbon electrode, it can also be a printed electrode and so on, the material of electrode matrix can be plastic, glass, paper and so on.

Usually, an electrochemical detection electrode can only detect one type of substance, and it may be difficult to detect more than one type of substance. The applicable range is therefore limited.

In addition, an electrochemical detection electrode is usually obtained by embellishment through a chemical process, an electrochemical detection electrode thus obtained can be nonuniform, therefore it is difficult for mass production.

At least one embodiments of the present disclosure can provide an electrochemical detection electrode and manufacturing method thereof and an electrochemical detection apparatus, the electrochemical detection electrode can realize the function of detecting more than one type of substance respectively, the detection efficiency is higher, the detection sensitivity is high, and uniformity is good, it can be utilized widely.

In an aspect of the present disclosure, an electrochemical detection electrode can be provided.

For example, the electrochemical detection electrode according to some embodiments can include a plurality of electrode structures, and a plurality of groups of detection structures on the plurality of electrode structures.

Specifically, the plurality of groups of detection structures include a first group of detection structures and a second group of detection structures, each of the first group of detection structures on one of the plurality of electrode structures having a first shape in a plane parallel to a surface of one of the plurality of electrode structures is configured to combine with a first detection object, each of the second group of detection structures on one of the plurality of electrode structures having a second shape in a plane parallel to a surface of one of the plurality of electrode structures is configured to combine with a second detection object.

In some embodiments, the first shape is different from the second shape.

In some implementations, the electrochemical detection electrode can include an electrode structure, the electrode structure can have multiple groups of detection grooves of different shapes, the multiple groups of detection groves of different shapes can be provided to be combined with detection objects of different shapes during a detection process.

That is, the plurality of groups of detection structures according to some embodiments are a plurality of detection grooves integrated on the plurality of electrode structures.

FIG. 1 is a perspective exemplary view of an electrochemical detection electrode 100 according to some embodiments of the present disclosure. As illustrated in FIG. 1, the electrochemical detection electrode 100 can include an electrode structure 110 or body, wherein the electrode structure 110 can further include multiple groups of detection grooves having various cross-sectional shapes, for example, a first set of detection grooves 111 having a first cross-sectional shape and second set of detection grooves 112 having a second cross-sectional shape.

The first cross-section shape and the second cross-section shape can be different, and as illustrated in this example are triangle and square, respectively.

In some embodiments, the plurality of detection grooves have a shape of a triangle, a diamond, a rectangle, or a circle.

The electrochemical detection electrode can have a plurality of detection regions, wherein multiple groups of detection grooves of different shapes are respectively located in different detection regions.

For example, the plurality of detection regions comprises a first detection region, a second detection region, and a third detection region.

In some implementations, a surface of the electrode structure in the first detection region can be covered by a graphene film layer.

In some implementations, a surface of the electrode structure in the second detection region can be covered by a diamond-like carbon film layer.

In some implementations, a surface of the electrode structure in the third detection region can be covered by a diamond film layer.

In some embodiments, the second detection region includes a plurality of detection sub-regions; and characteristics of the diamond-like carbon film in at least two detection sub-region are different.

In some embodiments, the electrode structure includes a plurality of sub-structures; and the detection grooves can be formed over the surfaces of the sub-structures.

In some embodiments, the plurality of sub-structures are provided in a form of an array or in a form of a stack structure.

In some embodiments, the plurality of sub-structures can have a shape of a cube, a cuboid, or a cylinder.

In some embodiments, the electrochemical detection electrode 100 can be a working electrode, wherein the electrochemical detection electrode 100 can be placed in a reaction solution.

When in the reaction solution, another substance can be placed in the reaction solution over the electrochemical detection electrode 100 and an Oxidoreduction reaction can occur with the substance to be detected in the reaction solution and a corresponding electric signal, for example, an electrical current, can be generated.

The substance to be detected can be determined based on the characteristics of the electric signal. For example, whether a particular component is present in the substance, whether the substance to be detected is a desired substance, the concentration of the desired substance, contaminants in the substance to be detected.

In some embodiments, the material of the electrode structure 110 can be metal, for example, gold or silver, glassy carbon, or any other suitable material. As such, there are no limitations herein with regard to a particular substance forming the electrode structure 110.

Further, while the embodiments discussed herein are illustrated as various geometric shapes, there are also no specific requirements with regard to the shape of the electrode structure 110.

For example, the electrode structure can be provided as a cube, cuboid, or any other shape.

For example, the electrode structure 110 can be a simple structure or a structure including a plurality of sub-structures, there are no limitations herein.

In some embodiments, and as illustrated herein, the first set of detection grooves 111 having the first shape, and the second set of detection grooves 112 having the second shape can be provided on the surface of the electrode structure 110.

For example, the electrochemical detection electrode 100 can include a plurality of detection regions, for example, a first detection region 001 and a second detection region 002, each having associated groups or sets of detection grooves having different shapes, wherein each set can be respectively located in different detection regions.

For example, the shape of the opening, e.g., the shape of the plane over the surface of the electrode structure 100, of a first set of detection grooves 111 can be a triangle and can be located in the first detection region 001, the second set of detection grooves 112 can be provided as a rectangle and can be located in the second detection region 002.

Figure 2A:
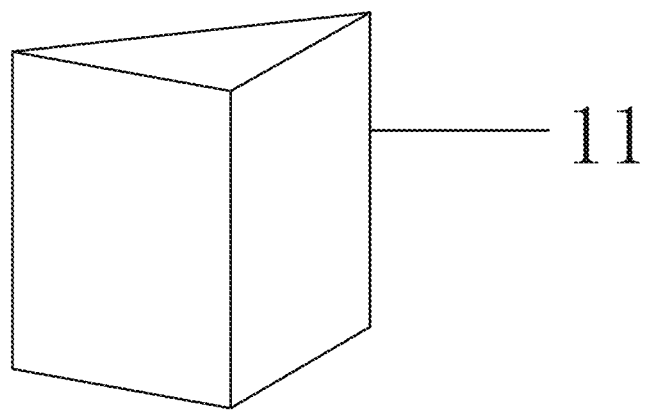
FIG. 2A illustrates a perspective view of an exemplary first detection carrier for use in conjunction with an electrochemical detection electrode according to various embodiments of the present disclosure.
Figure 2B:
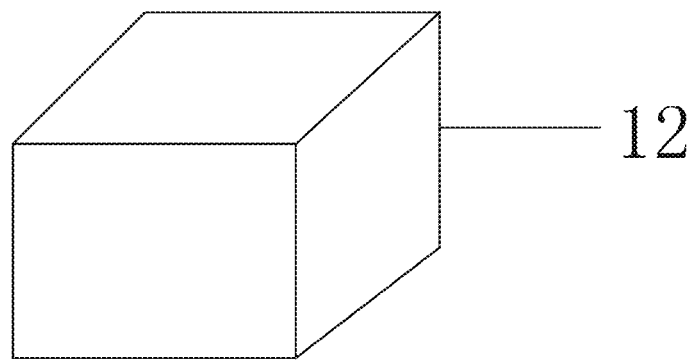
FIG. 2B illustrates a perspective view of an exemplary second detection carrier combined for use in conjunction with an electrochemical detection electrode according to some embodiments of the present disclosure.

A first substance to be detected, for example, glucose, and a second substance to be detected, for example, uric acid or purine trione, can be provided in the reaction solution so as to work together with the electrochemical detection electrode 100. As such, the first substance to be detected can be combined on a first detection carrier 11 which has a cross-section of a triangle, as shown in FIG. 2A, so as to form a first detection object, the second substance to be detected can be combined on a second detection carrier 12, having a cross-section of a rectangle, as shown in FIG. 2B, so as to form a second detection object.

When the electrochemical detection electrode 100 is placed in a reaction resolution, according to geometric shape matching principle, the first detection object can be combined with the first shape detection grooves 111, and similarly, the second detection object can be combined with the second shape detection grooves 112.

Oxidoreduction reaction can then be caused to occur in the respective regions, wherein the first substance to be detected in the first detection object and the second substance to be detected in the second detection object is placed over the surface of the electrode structure 110 and corresponding electric currents can be generated. Different sweep voltages can then be applied to the first detection region 001 and second detection region 002 of the electrode structure 110 through a detection circuit configured separately.

As a result, the electric current resulting from the reaction of the first substance to be detected and the electric current resulted from the reaction of the second substance to be detected can be respectively obtained and determined. Based on these associated electric currents, the function of detecting different substances can thus be realized. The electrochemical detection electrode 100 as illustrated here is capable of high detection efficiency, high detection sensitivity, and can be applied in a wide variety of situations.

In some embodiments, the portions of the electrode 110 where detection grooves of different shapes are located can be insulated from each other through an insulating layer provided therebetween which can be provided as part of the electrode structure.

For example, the portion of the electrode structure 110 that is located at the first detection region 001 is insulated from the portion of the electrode structure 110 that is located at the second detection region 002, as a result, the different portions of the electrode structure 110 each having detection grooves of different shapes can conduct detection separately.

Thus, the function of detecting different substances can be realized utilizing even a common electrode structure.

In some embodiments, the body of the detection electrode can be made of an imprinted material having a specific molecularly.

Molecularly imprinted material, or molecularly imprinted polymers, can be described as a material that has the characteristics of specific recognition and selective absorption. Such materials can selectively absorb one or more specific substances.

For example, the molecularly imprinted material for the first detection carrier 11 and the second detection carrier 12 can be different, such that the first detection carrier 11 can only absorb the first substance to be detected, for example, glucose, and the second detection carrier 12 can only absorb the second substance to be detected, for example, uric acid or purine trione.

As a result, different substances to be detected can be absorbed into respective detection carriers having associated different shapes.

In some embodiments, the detection carrier can be prepared utilizing various suitable methods, for example, detection carriers can be manufactured through molds or templates of specific shapes.

In some such embodiments, first, nanospheres emulsion can be added into molds or templates of different shapes; then, nanospheres emulsion now located in molds or templates of different shapes can be sintered into detection carriers having different desired shapes.

In some embodiments, the electrode structure 110 can be manufactured through a coining process, a printing process, or a photolithography process.

In an example, the photolithography process commonly used in microelectronics technologies can be employed, for example to form a plurality of protrusions on the surface of the electrode to thereby increase the surface area of the electrode.

The protrusions can have different shapes, can be uniformly distributed, or in a non-uniform distribution.

For example, in some embodiments, a UV sensitive material, for example, a photoresist, can be printed in the first detection region 001 of the electrode structure 110.

Next, a different material, which can be sensitive to visible light, for example, denatured vinyl ester resin, can be printed in the second detection region 002 of the electrode structure 110. Then, light emitted by a light source, such as a mercury lamp light source, can be divided into two paths by a filter, one path can be ultra-violet light, and the other path can be visible light.

The ultra-violet (UV) light can be directed so as to reach the UV sensitive material in the first detection region 001, and a triangle pattern can be formed utilizing a mask. In contrast, the visible light can be directed so as to reach the material sensitive to visible light in the second detection region 002, and a rectangle pattern can be formed with a mask.

In some additional embodiments, the first set of detection grooves 111 and the second set of detection grooves 112 can be formed through an etching process.

Of course, there are no limitations herein, the electrode structure 110 and/or the detection grooves can also be manufactured through other processes. For example, the electrode structure 110 and/or the detection grooves can be manufactured through a microelectronic lithography process, a 3D/4D printing, a mechanical machining process, a specific machining process, a laser cutting or etching process, a physical self-assembly or chemical self-assembly process, or by utilizing a combination of any one of the abovementioned processes.

For example, the electrochemical detection electrode can have its sub-structures as three-dimensional cavities, which can be formed by 3D printing.

The three-dimensional cavities can allow reaction solutions percolate therein, thereby increasing the contact surface area, improving the detection sensitivity. For example, the specific surface area of the electrode material can be significantly increased for the chemical reactions at the surface, increasing the electrical current amplitude in the electrochemical oxidoreduction reaction, thereby improving the detection sensitivity.

Some such processes can allow for the creation of a plurality of electrochemical detection electrodes 100 which have better uniformity and can also be more suitable for mass production.

It will then be appreciated that, "3D printing" refers to forming a multiple-layer three-dimensional structure through a method similar to printing, thus forming the electrode structure 100 and the detection grooves over it.

"4D" printing refers to forming a multiple-layer three-dimensional structure through a method similar to printing, and the material that forms the structure is sensitive to some parameters such as temperatures or PH values. Therefore, under different conditions, the structure can be three-dimensional and the material is sensitive, thus it can have the characteristic of a 4D structure, that is, in addition to spatial characteristics, it can also have other physical or chemical characteristics.

It will be appreciated that "3D printing" can also refer to any number of other additive material manufacturing methods as will be recognized by those having skill in the art.

It should be noted, according to embodiments of the present disclosure, the detection grooves of different shapes can be divided into multiple groups, and is not limited to only two groups, as illustrated in the drawings.

For example, the structure can also be provided having three groups, four groups, and so on. In addition, multiple groups of detection grooves each having different shapes, can be provided all over the surface of the electrode structure 110 at the same time. The detection grooves can also be provided respectively on all surfaces of the electrode structure 110 under different working conditions.

When multiple groups of detection grooves of different shapes are provided on various surfaces of the electrode structure 110 at the same time, more than one substance can similarly be detected at the same time. When multiple groups of detection grooves of different shapes are respectively provided on particular surfaces of the electrode structure 110 under different working conditions, different substance can be detected under different working conditions.

Wherein, "working conditions" refers to the conditions such as temperature, PH value or strength of electric field to which the electrochemical detection electrode 100 is exposed.

It should be noted, according to embodiments of the present disclosure, there are no limitations to the shapes of the openings of the detection grooves, for example, the opening of a detection groove can be a triangle, a diamond, a square, a rectangle, a circle, a star or any other shapes.

There are no limitations to the sizes of the openings of the detection grooves, it can be determined according to conditions of processes. For example, the sizes of the detection grooves can be of nanometer level or micrometer level, accordingly, the detection carriers shown in FIG. 2A and FIG. 2B can also be of nanometer level or micrometer level, such that the detection carriers can be combined with the detection grooves.

There are no limitations to the number of detection grooves, for example, the number of detection grooves can be determined according to the size of the electrode structure 110 and the sizes of the openings of the detection grooves, or the sizes of the grooves or apertures can be determined according to the detection accuracy implemented according to practical needs. For example, the aperture or groove size can be determined according to the strength of the electric current that can be detected.

Figure 3A:
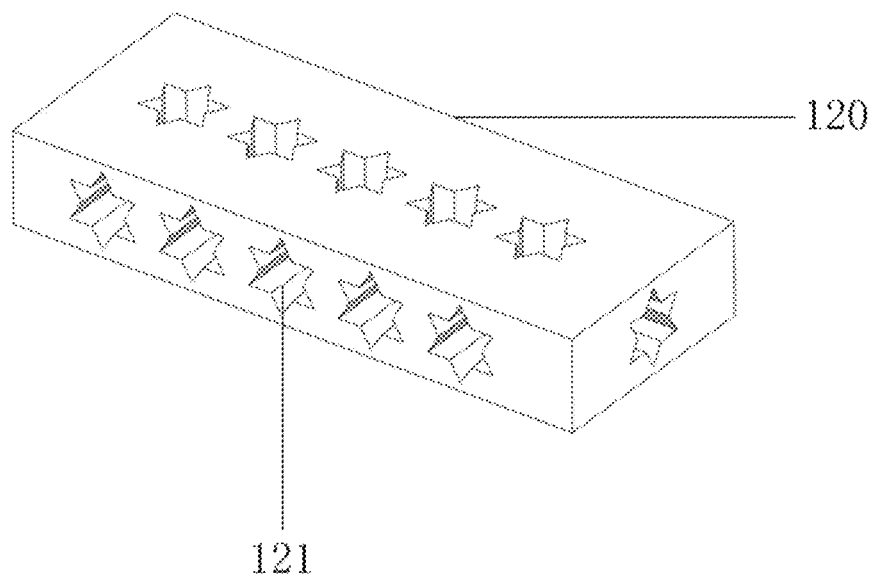
FIG. 3A illustrates a perspective view of an electrochemical detection electrode in a first state according to some embodiments of the present disclosure.
Figure 3B:
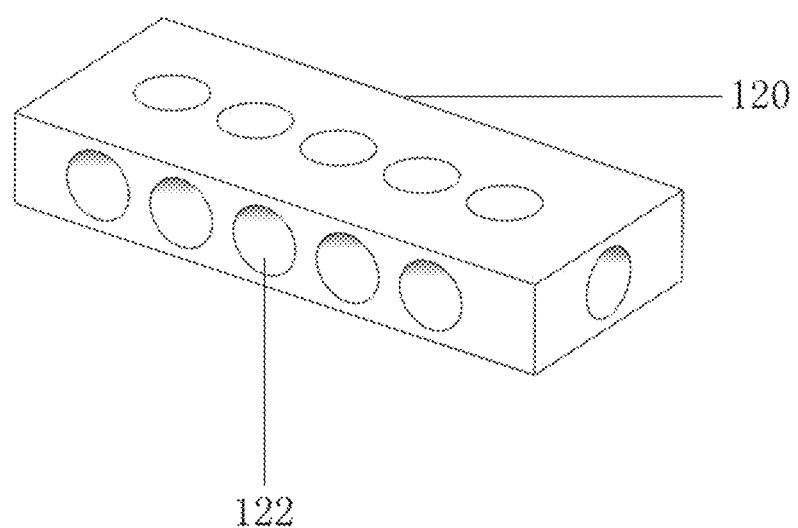
FIG. 3B illustrates a perspective view of an electrochemical detection electrode in a second state according to some embodiments of the present disclosure.

FIG. 3A and FIG. 3B are perspective views of two states of an electrochemical detection electrode according to some embodiments of the present disclosure. As shown in FIG. 3A and FIG. 3B, the electrode structure 120 of the electrochemical detection electrode 200 can have detection grooves of different preset shapes under different working conditions.

To function under different working conditions, for example, each of the plurality of groups of detection structures comprises a material of temperature memory or a material of pH sensitivity.

Specifically, the first group of detection structures can include a material of first temperature memory, each of the first group of detection structures has a first shape in the plane parallel to the surface of one of the plurality of electrode structures in a first temperature, and the second group of detection structures can include a material of second temperature memory.

Each of the second group of detection structures can have a second shape in the plane parallel to the surface of one of the plurality of electrode structures in a second temperature.

For example, the electrochemical detection electrode 200 can be made of memory alloy material, under a first working condition, for example, a first temperature T1. In such an embodiment, the electrode structure 120 can be provided having a third set of detection grooves 121, wherein the third set of detection grooves only manifest themselves under a second working condition, for example, a second temperature T2, wherein T2 is not equal to the first temperature T1. In such an embodiment the electrode structure 120 can also then be provided having a fourth set of detection grooves 122 which only appear under another working condition.

In some embodiments, the shapes of the opening of a third shape detection groove 121 and the shape of the opening of a fourth shape detection groove 122 can be different, wherein they can also be provided having various shapes, for example a star shape or a circular shape respectively.

When a particular reaction solution that works together with the electrochemical detection electrode 200 includes detection carriers which cross-sectional shapes are stars or circles and when different substances are absorbed by detection carriers of different shapes, the electrochemical detection electrode 200 can be respectively combined with detection carriers of star shapes or circular shapes under a first working condition and a second working condition.

In this manner, different substances absorbed by detection carriers having cross-sectional shapes are stars or circles can be respectively detected under a first working condition and a second working condition.

In some embodiments, the temperatures, PH values or strengths of electric fields can be different under a first working condition and a second working condition.

By changing working conditions, for example, the temperatures, PH values, or electric fields, strength of the reaction solution that surrounds the electrochemical detection electrode 200 can be changed. In this manner, the electrode structure 120 can be deformed to form at least one group of detection grooves having preset shapes under the working conditions.

For example, forming third shape detection grooves 121 or fourth shape detection grooves 122. In some embodiments, the electrode structure 120 can be manufactured utilizing a material that has time or temperature memory characteristics, PH value sensitivity or other sensitivity characteristics. These materials can then be selectively altered so as to provide associated differing structural characteristics in accordance with particular environmental parameters, which can be selectively changed.

For example, change in temperature change, change in PH value change, or change in strength of electric field, such that the electrode structure 120 can have detection grooves of different shapes under different working conditions.

In this manner, the functions of respectively detecting different substances can be realized.

In some embodiments, the plurality of electrode structures of the electrochemical detection electrode according can have a material of gelatin disposed thereover and configured to be deformed in response to an electric current applied thereto.

For example, the material of the electrode structure 120 can be gelatin, which is conductive and can be deformed. When different working voltages are applied, the shape of the surface of the electrode structure 120 can be changed, such that detection grooves of different shapes can be formed.

For example, gelatin that is conductive and can be deformed can be polyaniline (PANI), wherein PANI can be formed through utilizing nositol hexaphosphate (phytic acid) as a doping agent and cross-linking agent.

It should be noted that, according to embodiments of the present disclosure, the number of types of the shapes of the detection grooves at the surface of the electrode structure 120 under different working conditions can be two, three or any number.

Accordingly, the preset working conditions can also be two, three or any number. In order to realize the function of detecting different substances, as long as the working conditions, for example, changing the temperature, PH value or strength of electric filed of the reaction solution, are changed, the detection grooves over the surface of the electrode structure 120 can be deformed so as to become preset shapes. In this manner, the detection grooves can be combined with detection carriers of different shapes so as to allow detection of different substances absorbed over the grooves.

In some embodiments, the plurality of electrode structures include a first group of electrode structures and a second group of electrode structures. All of the first group of detection structures are on the first group of electrode structures, and all of the second group of detection structures are on the second group of electrode structures.

In some embodiments, each of the plurality of electrode structures comprises a first part and a second part, some of the first group of detection structures are on the first part, some of the second group of detection structures are on the second part.

In some embodiments, some of the first group of detection structures on the first part are a material of graphene film layer, some of the second group of detection structures on the second part are a material of a diamond film layer.

For example, each of the plurality of electrode structures can further include a third part, the plurality of groups of detection structures further include a third group of detection structures, some of the third group of detection structures on the third part are a material of diamond-like carbon film layer.

In some embodiments, the electrochemical detection electrode can further include a plurality of connection structures electrically connected to the plurality of electrode structures, wherein the plurality of connection structures are configured to transmit electric signals to the plurality of electrode structures and receive electric signals output by the plurality of electrode structures.

In implementations, the plurality of connection structures and the plurality of electrode structures can be in one-to one correspondence.

Figure 4A:
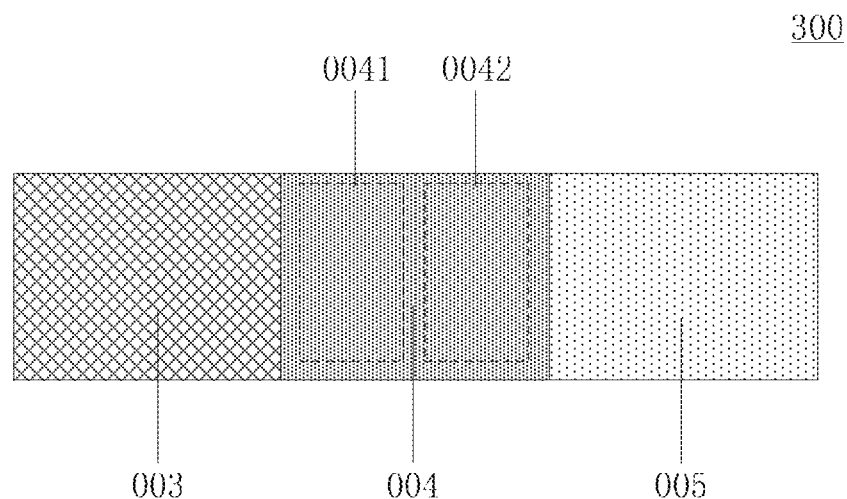
FIG. 4A illustrates a top plan view of an electrochemical detection electrode according to some embodiments of the present disclosure.
Figure 4B:
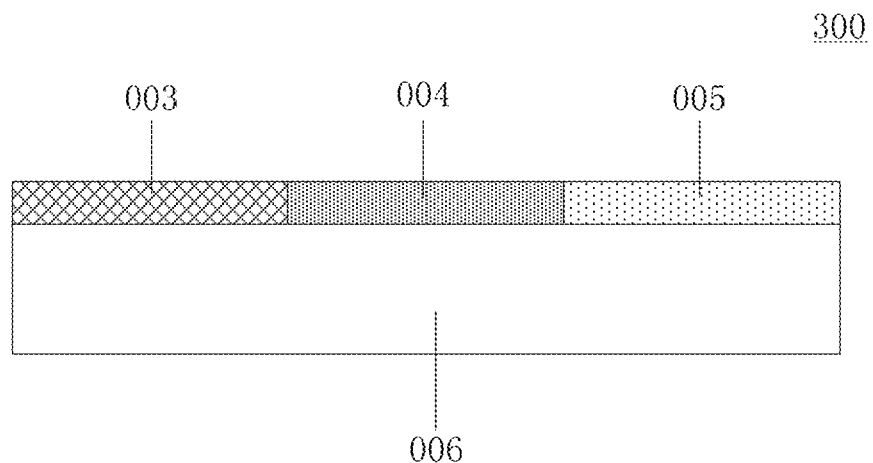
FIG. 4B illustrates a side cross-sectional view of the electrochemical detection electrode of FIG. 4A.

FIG. 4A illustrates a top view of an electrochemical detection electrode 300 according to some embodiments of the present disclosure, FIG. 4B is a cross-sectional view of the electrochemical detection electrode 300 of FIG. 4A.

As illustrated in FIG. 4A and FIG. 4B, the electrode structure of the electrochemical detection electrode 300 can include a plurality of detection regions. For example, a first detection region 003, a second detection region 004 and a third detection region 005.

As illustrated in this embodiment, the surface of the electrode structure in the first detection region 003 can be covered by a first substance, for example a graphene film layer, wherein the surface of the electrode structure in the second detection region 004 can be covered by a second substance, for example a diamond-like carbon film layer, and wherein the surface of the electrode structure in the third detection region 005 can be covered by a third substance, for example a diamond film layer.

It will then be appreciated that due to the various particular characteristics between the graphene material, the diamond-like carbon material, and the diamond material, that the associated respective micro-structures of the surfaces of the graphene film layer, diamond-like carbon film layer, and diamond film layer are also different.

In other words, detection grooves of different shapes can exist with respect to the graphene film layer, as opposed to the diamond-like carbon film layer, or the diamond film layer. Therefore, each of these substances can be combined with detection carriers absorbed with different substances of three different shapes to realize the function of detecting three different substances.

For example, in an embodiment, the first detection region 003 can be combined with detection carriers absorbed with glucose molecules, and thus glucose can be detected by utilizing the first detection region 003.

The second detection 004 can be combined with detection carriers absorbed with uric acid or purine trione molecules, thus uric acid or purine trione can be detected by utilizing the second detection region 004; and further, the third detection region 005 can be combined with detection carriers absorbed with triglyceride molecules, thus triglyceride can be detected by utilizing the third detection region 005.

The shapes of the different detection carriers absorbed with different substances are different, and the shapes of different detection carriers correspond to the shapes of micro-structures over the surfaces of the three detection regions, i.e. detection grooves, such that it is convenient that they can be combined respectively. As a result, the detection of three different substances can be realized.

In some embodiments, a graphene film layer, a diamond-like carbon film layer and a diamond film layer can be formed at different positions on an upper surface of a high-purity oriented graphite substrate 006, such as by utilizing a laser pulse manufacturing process.

In general, different materials of different structures can be obtained on the graphite substrate 006 by different processes. For example, such materials can include graphene, diamond, and diamond-like carbon. Among these different materials, the diamond-like carbon is a material between graphene and diamond, and its composition can be distinguished by spectral analysis.

By employing different processes, properties of the diamond-like carbon can also vary continuously, and be analyzed based on the continuously varying spectra.

Based on the continuously-varying material properties, methods for detecting similar substances, such as chirality substances, fatty acids of different chain lengths, and structurally-similar compounds, can be developed.

The method can also be used for purification and separation of samples, which can be analyzed with chromatography.

In this manner, the first detection region 003, the second detection region 004, and the third detection region 005 can be formed. Further, this allows for the manufacturing process to be simplified through this method, as will be appreciated by those of ordinary skill in the art. Of course, there are no limitations herein, the graphene film layer, diamond-like carbon film layer and diamond film layer can also be formed through other known or otherwise recognized processes.

Figure 4C:
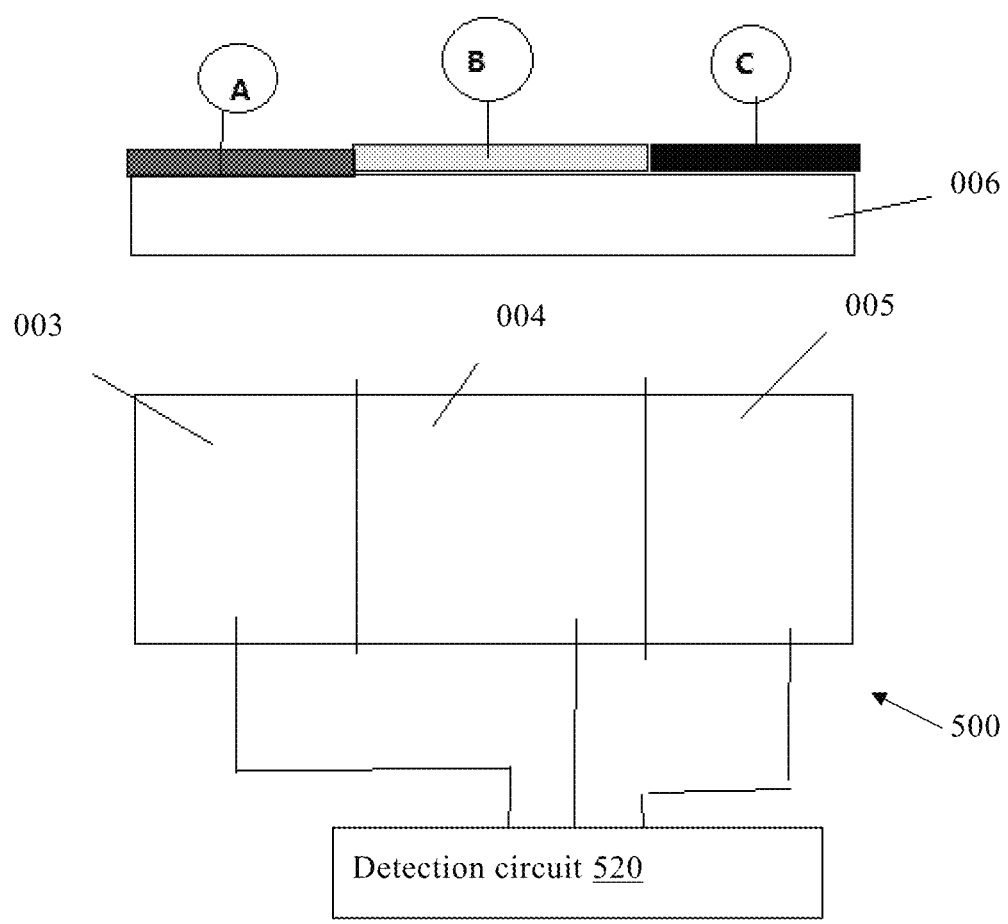
FIG. 4C is a schematic diagram illustrating a detection apparatus including a detection circuit configured to detect or quantify the different target substances.

FIG. 4C is a schematic diagram illustrating a detection apparatus 500 including a detection circuit 520 configured to detect or quantify the different target substances.

As shown, target substances A (e.g., glucose), B (e.g., uric acid or purine trione), and C (e.g., triglicyride) can be respectively detected or have their quantities measured at the first, second, and third detection regions 003, 004, 005.

The first, second, and third detection regions 003, 004, 005 can be respectively the graphene region, the diamond-like film region, the diamond film region formed over the high-purity oriented graphite substrate 006.

As has also been recognized, diamond-like carbon is a material having characteristics similar to graphene and diamond, wherein the characteristics of diamond-like carbon can change continuingly.

In some embodiments, the characteristics of different portions of the diamond-like carbon film layer can be altered through controlling the fabrication process. Thus, the second detection region 004 can further include a plurality of detection sub-regions.

For example, in an embodiment, the second detection region 004 can include a plurality of detection sub-regions, for example a first detection sub-region 0041 and a second detection sub-region 0042, wherein the characteristics of the diamond-like carbon film of at least two detection sub-regions are different. For example, the first detection sub-region 0041 and the second detection sub-region 0041 can both be covered by diamond-like carbon film.

However, the characteristics the of the diamond-like carbon film of the first detection sub-regions 0041 and the second detection sub-region 0042 are different. As a result, the shapes of the detection grooves of the surface of the diamond-like carbon film layer in the first detection sub-region 0041 will correspondingly be different from the shapes of the detection grooves of the surface of the diamond like-carbon film in the second detection sub-region 0042.

In this manner, varying detection sub-regions can be combined with detection carriers of different shapes, thus the function of detecting different substances can be realized.

It should be noted, according to embodiments of the present disclosure, the number of detection sub-regions in the second detection region 004 that is covered by diamond-like film is not limited, and can be any number.

For example, the plurality of detection sub-regions can be utilized to detect substances with similar characteristics, for example, chiral compounds, fatty acids with different chain lengths, compounds with similar structures and so on. The electrochemical detection electrode 300 can thus be utilized to purify and separate samples, for example, chromatographic analysis.

Figure 5A:
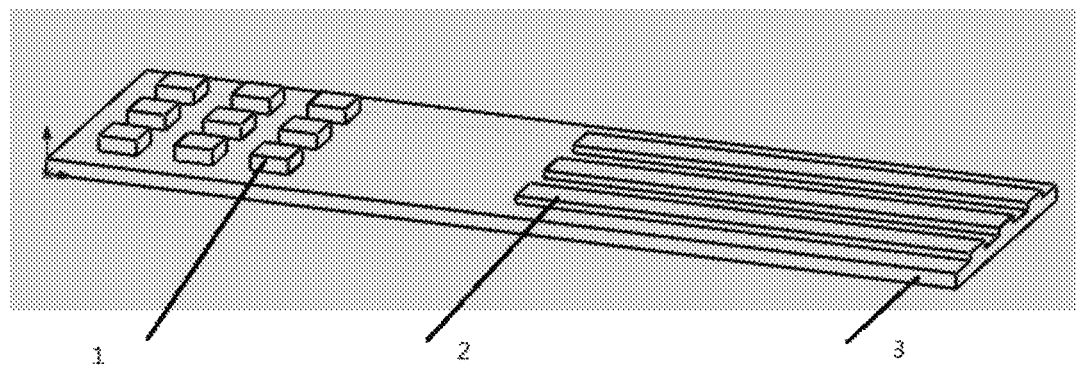
FIG. 5A illustrates a perspective view of an electrochemical detection electrode according to some embodiments of the present disclosure.

FIG. 5A illustrates a perspective view of an electrochemical detection electrode according to some embodiments of the present disclosure, including array electrodes 1, electrode connections 2, and substrate 3. The array electrodes 1 can include a plurality of protrusions forming an array.

Figure 5B:
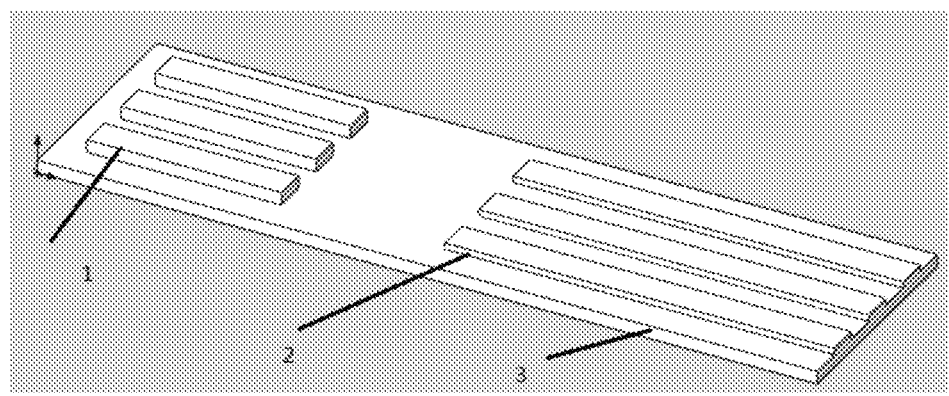
FIG. 5B illustrates a perspective view of an electrochemical detection electrode according to some other embodiments of the present disclosure.

FIG. 5B illustrates a perspective view of an electrochemical detection electrode according to some other embodiments of the present disclosure, including array electrodes 1, electrode connections 2, and substrate 3. The array electrodes 1 can include a plurality of elongated protrusions substantially along the same direction as the electrode connections 2.

Figure 5C:
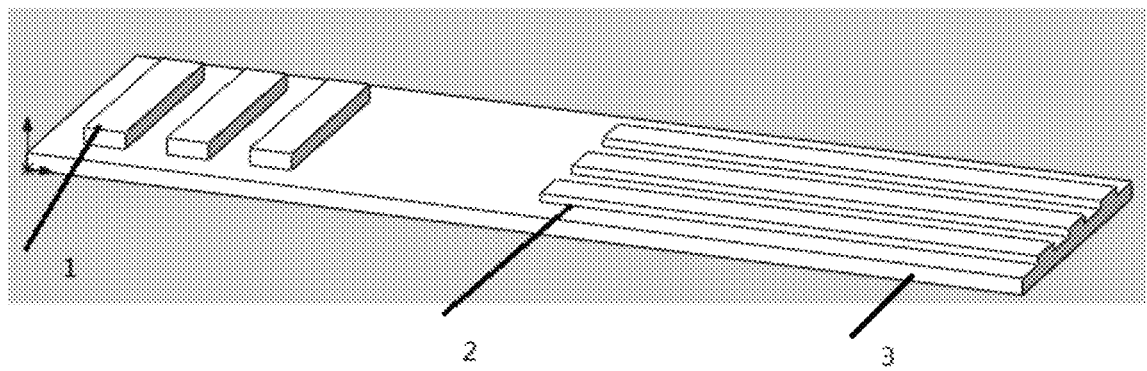
FIG. 5C illustrates a perspective view of an electrochemical detection electrode according to some other embodiments of the present disclosure.

FIG. 5C illustrates a perspective view of an electrochemical detection electrode according to some other embodiments of the present disclosure including array electrodes 1, electrode connections 2, and substrate 3. The array electrodes 1 can include a plurality of elongated protrusions in a direction transverse to the direction of the electrode connections 2.

Figure 5D:
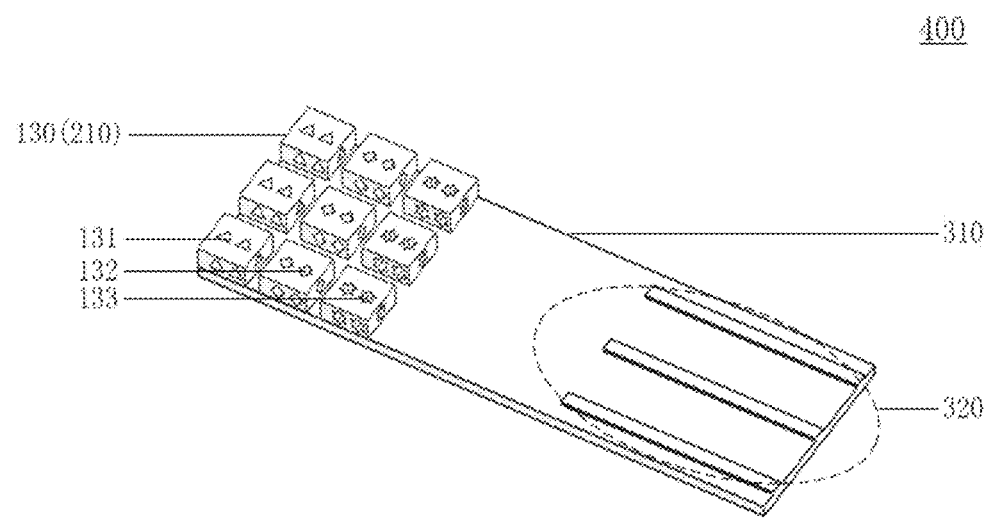
FIG. 5D illustrates a perspective view of an electrochemical detection electrode according to some other embodiments of the present disclosure.

FIG. 5D illustrates an exemplary perspective view of an electrochemical detection electrode 400 according to some embodiments of the present disclosure.

As illustrated in FIG. 5D, the electrochemical detection electrode 400 can include a substrate 310, a connection structure 320 and an electrode structure 130. The electrode structure 130 can include a plurality of sub-structures 210.

The substrate 310 can be utilized to provide support and protection.

The substrate 310 can be made of virtually any material, but some advantages are provided by using plastic, glass, or paper, however any other suitable material can also be utilized which may be suitable for any particular application.

The electrode structure 130 and the connection structure 320 can both be provided over the substrate 310. The connection structure 320 and the electrode structure 130 can be electrically connected through conductive wires (not shown in figures), wherein the connection structure can be provided to transmit electric signals to the electrode structure 130 or receive electric signals outputted from the electrode structure 130.

The material of the connection structure can be any suitable conductive material, for example, metal material such as silver, silver chloride, or platinum or intermetallic compounds.

The electrode structure 130 can include a plurality of sub-structures 210. For example, the shapes of the sub-structures 210 can be cubes, the plurality of sub-structures 210 can be arranged in the form of an array. The detection grooves can be formed over the surfaces of the sub-structures 210.

For example, the shapes of the openings of the first shape detection grooves 131, the second shape detection grooves 132, and the third shape detection grooves 133 can be different and respectively located at the surfaces of different sub-structures 210.

The shape detection grooves can be combined with corresponding types of detection carriers of different shapes, thus the detection of multiple types of substance can be realized, herein illustrated as three types of substances. For example, the plurality of sub-structures 210 with first shape detection grooves 131 can be electrically connected to one another through conductive wires, wherein the plurality of sub-structures 210 with second shape detection grooves 132 can be electrically connected to one another through conductive wires, and finally the plurality of sub-structures 210 with third shape detection grooves 133 can be electrically connected to one another through conductive wires.

Further, the sub-structures 210 with detection grooves of different shapes can be insulated from one another, therefore, three paths of independent electric signal can be obtained, and the function of detecting multiple, herein illustrated as three, types of substances can be realized.

Through providing the sub-structures 210, the surface area of the electrode structure 130 can be effectively increased, the contact area between the electrode structure 130 and the detection objects in the reaction solution can be increased. As a result, the electric current generated during the process of oxidoreduction reaction of the substances to be detected in the detection objects can be improved, and correspondingly the detection sensitivity can be improved.

It should be noted, according to embodiments of the present disclosure, there are no limitations to the shapes of the sub-structures 210, they can be cubes, cuboids, or cylinders, they can also be three-dimensional cavities or any other shapes.

There are no limitations to the method of arrangement of the plurality of sub-structures 210, and the arrangement of sub-structures 210 can be determined or adjusted according to practical needs.

For example, the arrangement of sub-structures 210 can be determined according to processing conditions or processing methods. The plurality of sub-structures can be arranged uniformly, they can also be arranged nonuniformly.

Figure 6A:
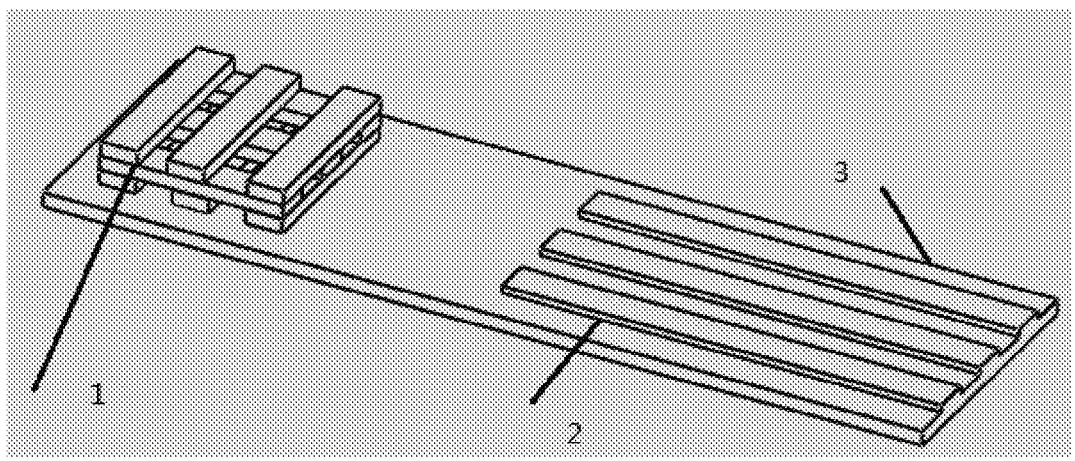
FIG. 6A illustrates a perspective view of another electrochemical detection electrode according to some embodiments of the present disclosure.

FIG. 6A illustrates a perspective view of another electrochemical detection electrode according to some embodiments of the present disclosure, including array electrodes 1, electrode connections 2, and substrate 3. The array electrodes 1 can include a plurality of elongated protrusions stacked in multiple layers, for example in alternating directions either along or transverse to the direction of the electrode connections 2.

The stacked array electrodes 1 therefore have a 3D structure, facilitating target substance detections and/or measurements in multiple layers in the 3D electrode structure.

Figure 6B:
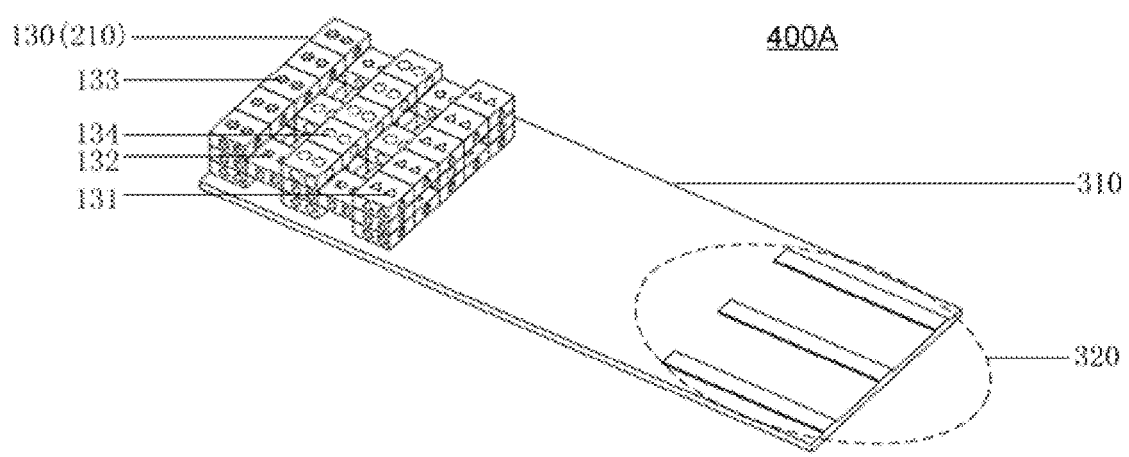
FIG. 6B illustrates a perspective view of the other electrochemical detection electrode according to some other embodiments of the present disclosure.

FIG. 6B is a schematic view of another electrochemical detection electrode 400A according to some other embodiments of the present disclosure.

As illustrated in FIG. 6B, the electrochemical detection electrode 400A can be similar to the electrochemical detection electrode 400 of FIG. 5D except the method of arrangement of the sub-structures 210 can be different and a fourth shape detection groove 134 can be provided.

According to some embodiments of the present disclosure, the plurality of sub-structures 210 can also be a stack structure. The first shape detection grooves 131, the second shape detection grooves 132, the third shape detection grooves 133, and the fourth shape detection grooves 134 can be respectively located on the surfaces of different sub-structures 210.

The surface area of the electrode structure 130 of the electrochemical detection electrode 400A is large, and correspondingly the detection sensitivity is high, while also allowing for the detection of four different types of substances.

For example, the sub-structures 210 can be made of gelatin that is conductive and can be deformed, when the working voltage applied to the sub-structures 210 is changed, the plurality of sub-structures 210 can be deformed into a stack structure.

The gelatin can react to the electric field to form various three-dimensional structures, thereby increasing the surface area and improving the detection sensitivity.

For example, the sub-structures 210 with detection grooves of different shapes can be insulated from one another when an insulating layer, (not shown in figures), is provide among the sub-structures 210 with detection grooves of different shapes As a result, the electric signals respectively generated by them will not interfere with one another.

Figure 7:
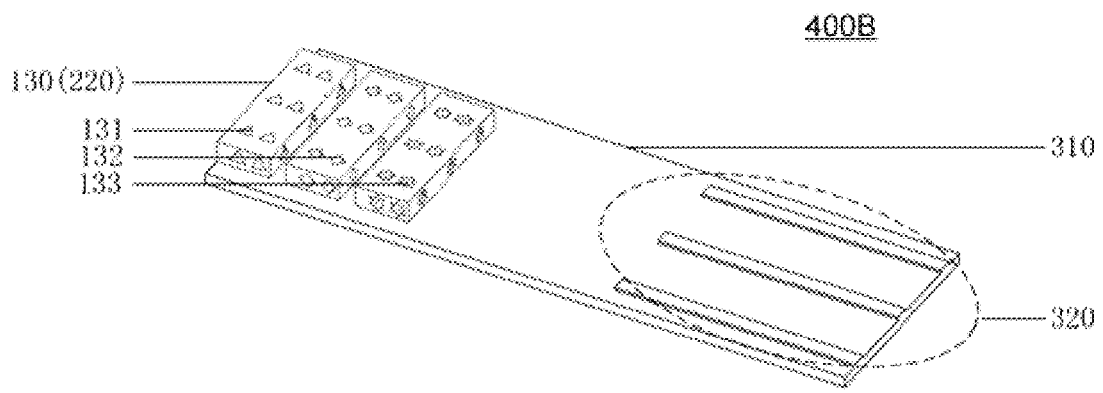
FIG. 7 illustrates a perspective view of yet another electrochemical detection electrode according to yet some other embodiments of the present disclosure.

FIG. 7 is a schematic view of yet another electrochemical detection electrode 400B according to yet some other embodiments of the present disclosure. As illustrated in FIG. 7, the electrode structure 130 can include a plurality of sub-structures 220 in cuboid shape.

The plurality of sub-structures 220 can be arranged in the same row, wherein detection grooves of different shapes can be located on the surfaces of different sub-structures 220. Other characteristics of the electrochemical detection electrode 400B are basically the same as the electrochemical detection electrode 400 of FIG. 5D, and as such will not be repeated herein.

Figure 8:
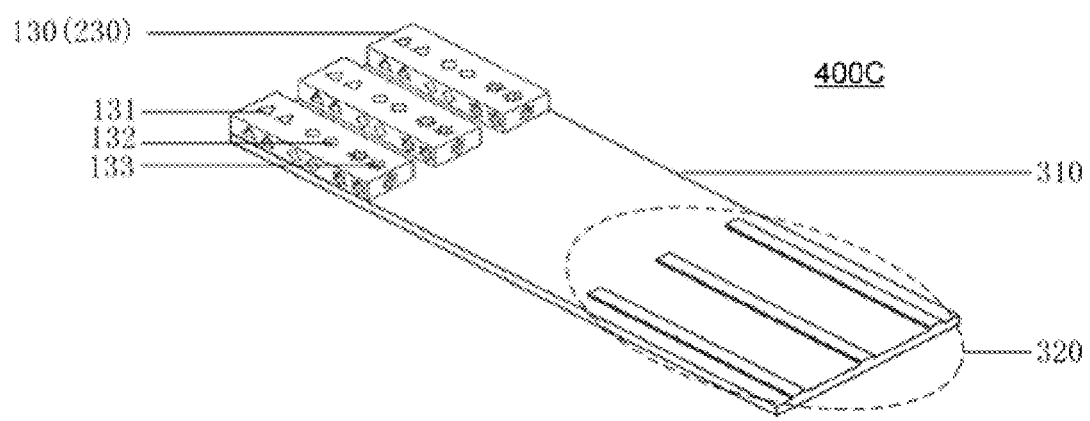
FIG. 8 illustrates a perspective view of yet another electrochemical detection electrode according to yet some other embodiments of the present disclosure.

FIG. 8 is a schematic view of yet another electrochemical detection electrode 400C according to yet some other embodiments of the present disclosure.

As illustrated in FIG. 8, the electrode structure 130 can include a plurality of sub-structures 230 having cuboid shapes.

As illustrated here, the plurality of sub-structures 230 can be arranged in the same row. For example, detection grooves of different shapes can be provided over different positions of the same sub-structure 230, wherein each different position can be insulated from one another through an insulating layer provided separately, (not shown in figures), thus the electric signals generated by different positions of the sub-structure 230 will not interference with one another.

Other characteristics of the electrochemical detection electrode 400C can be similar to the electrochemical detection electrode 400 of FIG. 5D, and as such will not be repeated herein.

Figure 9A:
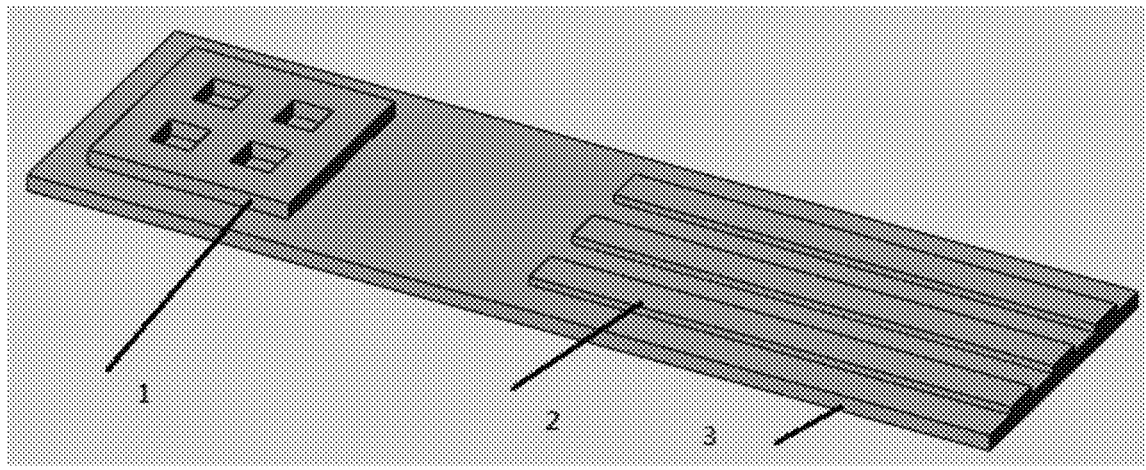
FIG. 9A illustrates a perspective view of yet another electrochemical detection electrode according to yet some other embodiments of the present disclosure.

FIG. 9A illustrates a perspective view of yet another electrochemical detection electrode according to yet some other embodiments of the present disclosure, including array electrodes 1, electrode connections 2, and substrate 3. The array electrodes 1 can include a plurality of indentations forming an array.

Figure 9B:
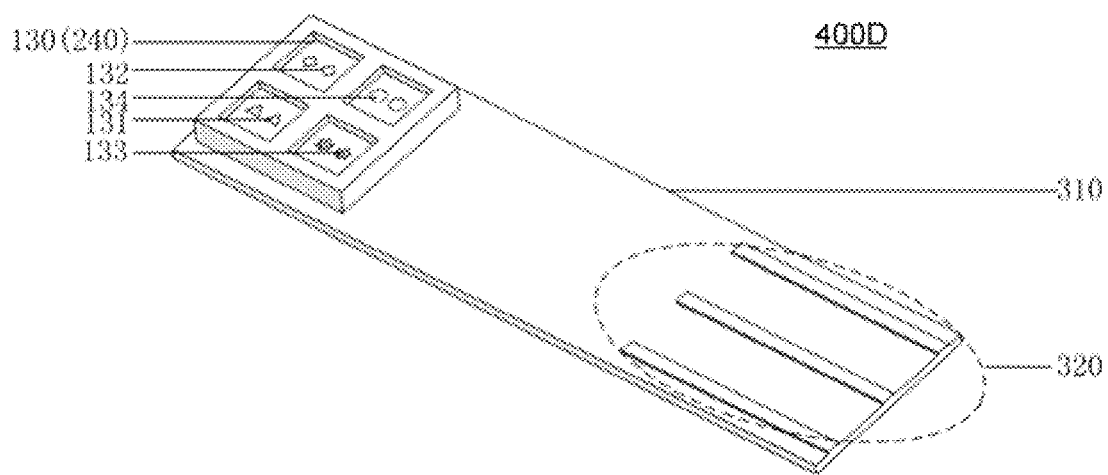
FIG. 9B illustrates a perspective view of yet another electrochemical detection electrode according to yet some other embodiments of the present disclosure.

FIG. 9B is a schematic view of yet another electrochemical detection electrode 400D according to yet some other embodiments of the present disclosure.

As illustrated in FIG. 9B, the electrode structure 130 can include a plurality of sub-structures 240, the sub-structures 240 can be three-dimensional cavities.

For example, "a three-dimensional cavity" refers to an indentation region located over the surface of the electrode structure 130. The first shape detection grooves 131, the second shape detection grooves 132, the third shape detection grooves 133 and the fourth shape detection grooves 134 can be respectively located at the surfaces of different sub-structures 240, in other words, located in different indentation regions of the electrode structure 130.

In some embodiments, detection grooves can be provided at both the bottom and the side wall of the indentation region. In the figures, only the detection grooves provided at the bottom of the indentation region are shown, however, detection grooves can also be provided about a side wall of the indentation region, but are not shown.

During the working process, the reaction solution can enter the indentation regions, thus, the contract area between the electrode structure 130 and the detection object in the reaction solution can be increased, and the detection sensitivity can be improved.

It should be noted, according to embodiments of the present disclosure, there are no limitations to the shapes of the indentation regions, they can be cubes, cuboids, circles or any other shapes. Other characteristics of the electrochemical detection electrode 400D are similar to the characteristics of the electrochemical detection electrode 400 of FIG. 5D, and as such will not be repeated herein.

In another aspect of the present disclosure, an electrochemical detection apparatus can be provided, including the electrochemical detection electrode of any one of the abovementioned embodiments of the present disclosure.

The electrochemical detection apparatus can realize the function of respectively detecting different types of substances, wherein the detection efficiency is high, the detection sensitivity is high, and uniformity is good thus allowing for a wide application range.

For example, electrochemical detection apparatus can include the electrochemical detection electrode and have multiple groups of detection carriers.

The multiple groups of detection carriers can be configured so as to be respectively utilized for surface adsorption of substances to be detected and combined with the multiple groups of detection grooves of different shapes of the electrochemical detection electrode during a detection process.

The shapes of cross-sections of the detection carriers can include, for example, triangles, diamonds, rectangles, or circles.

In some embodiments, the electrochemical detection apparatus can further include a detection circuit, wherein the detection circuit is electrically coupled to the electrochemical detection electrode.

In some implementations, the detection circuit is configured to transmit electric signals to the electrochemical detection electrode and receive electric signals output by the electrochemical detection electrode.

The electrochemical detection apparatus can further include a working condition controller configured to control working conditions of the electrochemical detection electrode.

The working condition controller can be configured to control at least one of temperature, PH value, or electric field strength.

Figure 10:
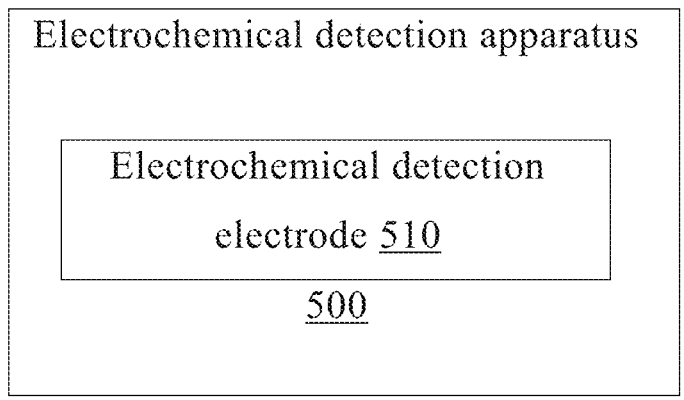
FIG. 10 illustrates a schematic view of an electrochemical detection apparatus utilizing any of the electrochemical detection electrodes discussed herein according to some alternative embodiments of the present disclosure.

FIG. 10 illustrates a schematic view of an electrochemical detection apparatus according to some embodiments of the present disclosure.

As illustrated in FIG. 10, the electrochemical detection apparatus 500 can include an electrochemical detection electrode 510, the electrochemical detection electrode 510 can be the electrochemical detection electrode according to any one of the abovementioned embodiments of the present disclosure, for example, the abovementioned electrochemical detection electrode 100/200/300/400.

The electrochemical detection apparatus 500 can be an electrochemical working station or any other electrochemical measurement system, and as such, there are no limitations herein. The electrochemical detection apparatus 500, for example, can be utilized in biotechnologies, qualitative or quantitative analysis of substances and so on.

In some embodiments, the electrochemical detection apparatus 500 can further include multiple groups of detection carriers, the multiple groups of detection carriers can respectively be utilized to absorb substances to be detected over their surfaces and to be combined with the multiple groups of detection grooves of different shapes of the electrochemical detection electrode 510.

Each group of detection carrier can include a plurality of detection carriers, for example, in an embodiment, the detection carriers can be as illustrated in FIG. 2A and FIG. 2B. of course, there are no limitations herein, the shapes of the cross-sections of the detection carriers can be triangles, diamonds, squares, rectangles, star-shape or any other suitable shapes, as long as the shapes of the detection carriers and the shapes of the detection grooves match each other such that it is convenient for combination.

For example, the substances to be detected can be any kind of substances, for example, can be glucose, uric acid, triglycerides and so on, there are no limitations herein. for example, molecular imprinting technique can be utilized such that different substances can be absorbed to the surfaces of different detection carriers. Detailed description of detection carrier has been provided in the content above, it will not be repeated herein.

Figure 11:
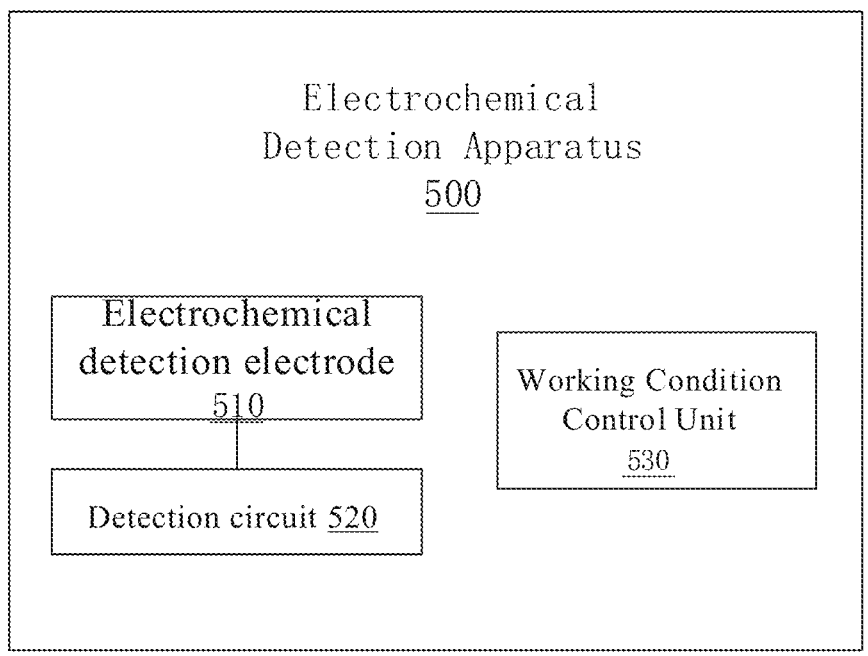
FIG. 11 illustrates a schematic view of another electrochemical detection apparatus also utilizing any of the electrochemical detection electrodes as discussed herein according to some other embodiments of the present disclosure.

FIG. 11 is a schematic view of another electrochemical detection apparatus according to some other embodiments of the present disclosure. As illustrated in FIG. 11, the electrochemical detection apparatus 500 can further include a detection electrode 520. The detection electrode 520 can be electrically connected to the electrochemical detection electrode 510.

In this manner, the detection electrode 520 can be provided as outputting electric signals to the electrochemical detection electrode 510 and/or receiving electric signals outputted by the electrochemical detection electrode 510. Detection results can then be obtained through processing of the electric signals.

Figure 12A:
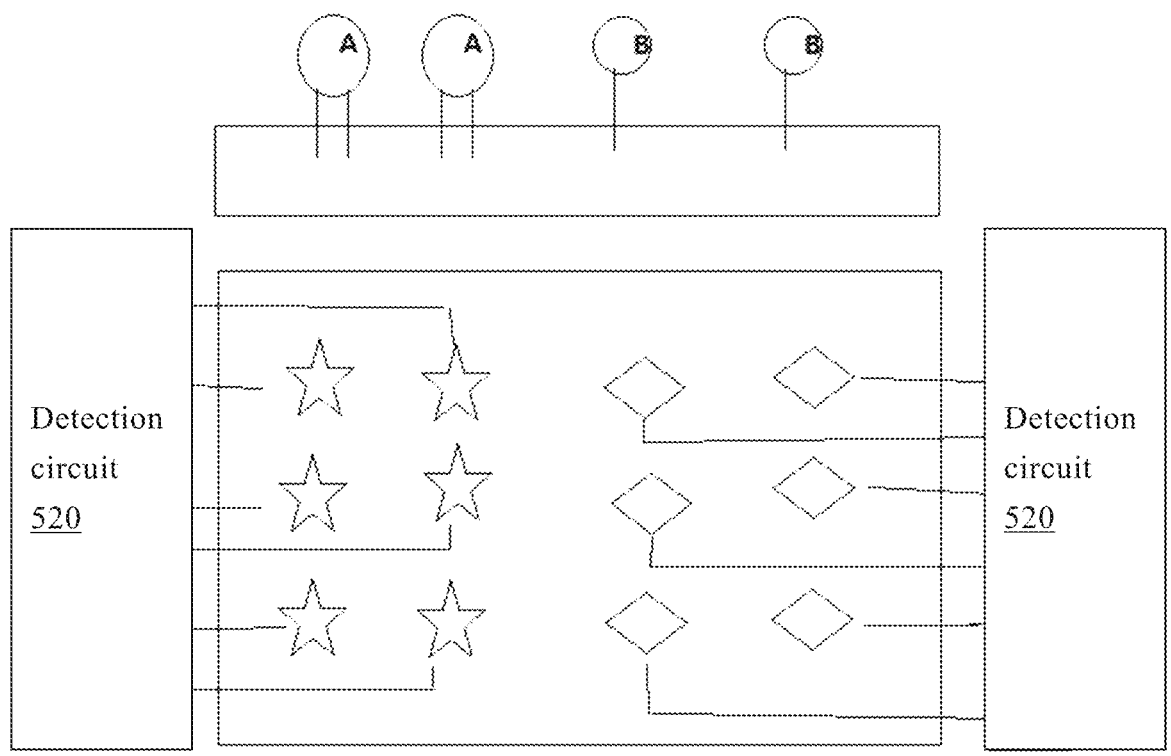
FIG. 12A illustrates a schematic view of yet another electrochemical detection apparatus according to yet some other embodiments of the present disclosure.

FIG. 12A illustrates a schematic view of yet another electrochemical detection apparatus according to yet some other embodiments of the present disclosure.

As shown, target substances A and B to be detected and/or measured respectively in a first electrode region having an electrode surface film patterned with a first shape, such as stars, and in a second electrode region having an electrode surface film patterned with a second shape, such as diamond shapes.

Figure 12B:
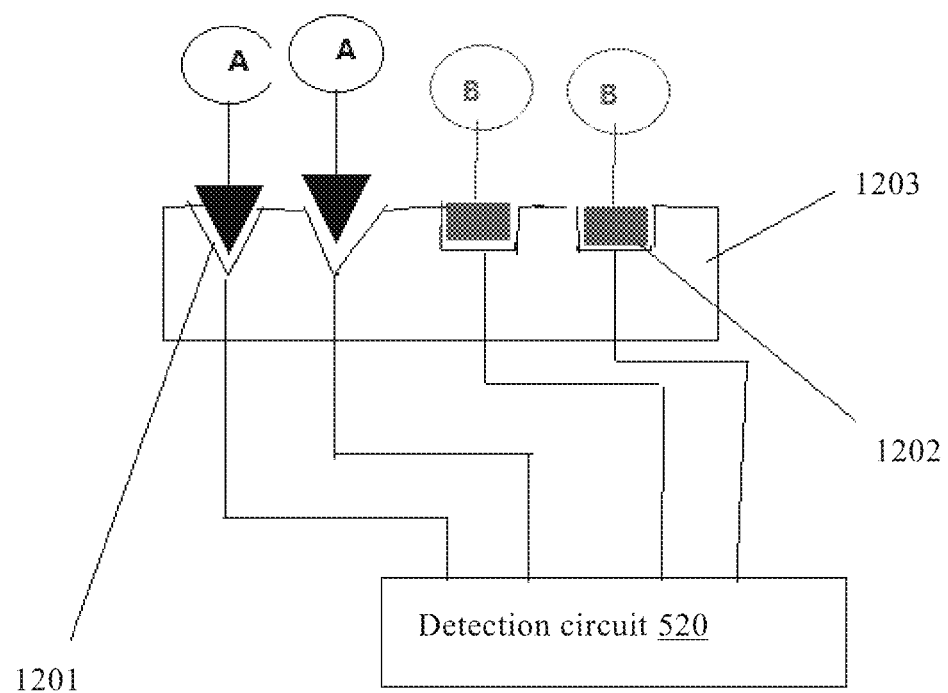
FIG. 12B illustrates a schematic view of yet another electrochemical detection apparatus according to yet some other embodiments of the present disclosure.

FIG. 12B illustrates a schematic view of yet another electrochemical detection apparatus according to yet some other embodiments of the present disclosure.

As shown, target substances A and B to be detected and/or measured respectively in a first electrode region having an electrode surface film patterned with a first microstructure 1201, such as having a cross section of triangles, and in a second electrode region having an electrode surface film patterned with a second microstructure 1202, such as having a cross section of rectangles or squares. The electrode substrate 1203 can carry a plurality of microstructures of different shapes.

The microstructures of different shapes can be configured to combine with different types of molecules, to thereby facilitate detection of different molecules at the different regions. For example, microspheres or microparticles with triangle shapes can be configured to combine with glucose molecules, and microparticles with diamond shapes can be configured to combine with uric acid molecules, etc.

Figure 12C:
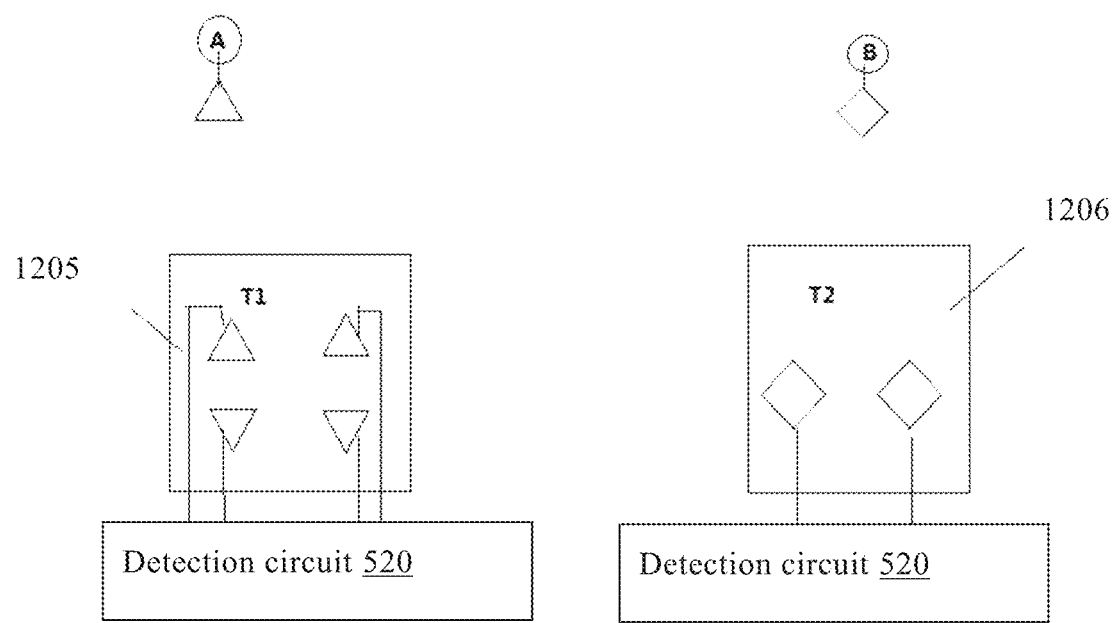
FIG. 12C illustrates a schematic view of yet another electrochemical detection apparatus according to yet some other embodiments of the present disclosure.

FIG. 12C illustrates a schematic view of yet another electrochemical detection apparatus according to yet some other embodiments of the present disclosure.

As illustrated, the electrode includes a first detection region 1205 and a second detection region 1206, respectively configured to detect/measure the first target substance A and the second target substance B. The first detection region 1205 and the second detection region 1206 can be on a same region of the electrode, and be respectively formed or switched therebetween based on a material memory property.

For example, the first detection region 1205 can form a first microstructure having a shape such as triangles at a first temperature T1. The second detection region 1206 can form a second microstructure having a shape such as diamond shapes at a second temperature T2.

By controlling the temperature of the electrode to T1, the electrode surface form the triangle-shaped microstructures as a result of the temperature memory. The triangle-shaped microstructures can be suitable for the detection/measurement of target substance A based on measured electrical signals at the detection circuit 520.

By controlling the temperature of the electrode to T2, the electrode surface form the diamond-shaped microstructures as a result of the temperature memory. The triangle-shaped microstructures can be suitable for the detection/measurement of target substance B based on measured electrical signals at the detection circuit 520.

As such, the different detection regions 1205, 1206 can be spatially distinguishing in the 3D detection structure of the detection electrode, and/or spatial-temporally distinguishing in the 4D detection structure of the detection electrode, such as by varying the temperature T1, T2 temporally.

In some other embodiments, the detecting structures can respond to other environmental parameters instead of (or in addition to) the temperatures. For example, the detecting structures can be configured to respond to acidity, measured by pH values. At a first pH value, the microstructures can have a first shape configured to detect a first target substance. At a second pH value, the microstructures can have a second shape configured to detect a second target substance.

Figure 12D:
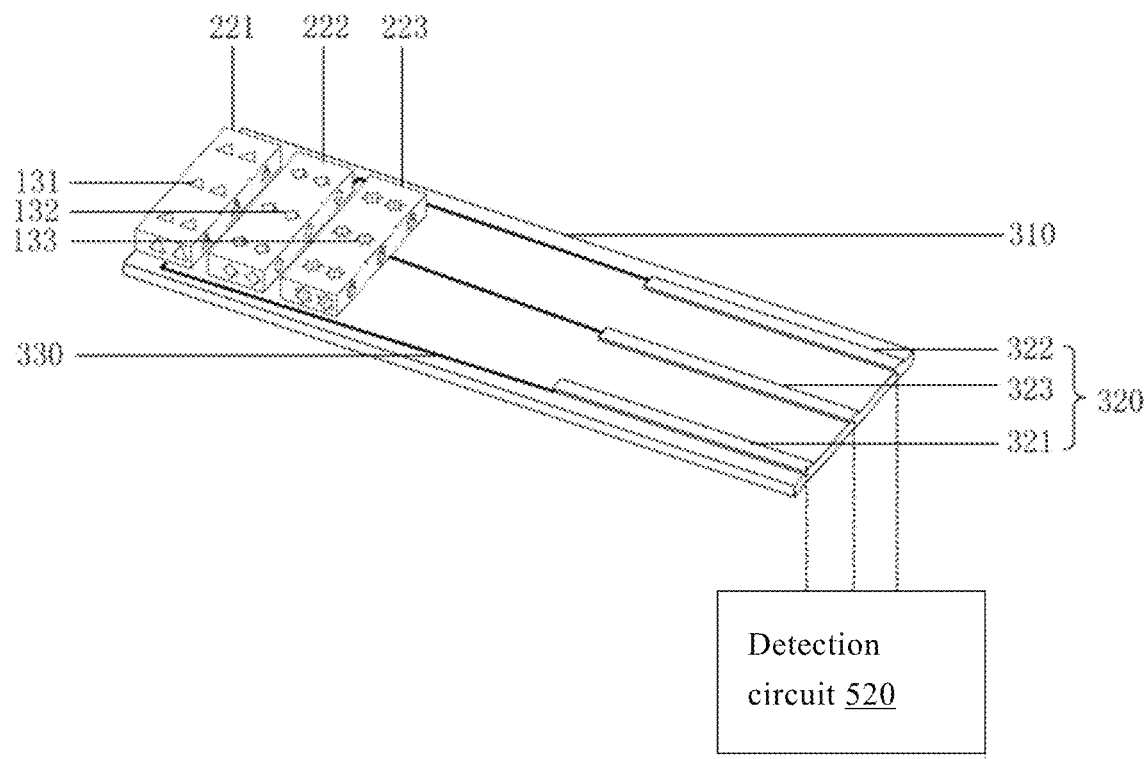
FIG. 12D illustrates a perspective view of yet another electrochemical detection apparatus according to yet some other embodiments of the present disclosure.

In some embodiments, as illustrated in FIG. 12D, a first sub-structure 221 with first shape detection grooves 131, a second sub-structure 222 with second shape detection grooves 132, and a third sub-structure 223 with third shape detection grooves 133 can be respectively electrically connected to first connection sub-structure 32.

In this manner, the second connection sub-structure 322 and the third connection sub-structure 323 of the connection structure 320 can be connected by means of three conductive wires 330, which then allows for the detection circuit 520 to have a plurality of channels wherein each channel can be respectively electrically connected to the first connection sub-structure 321, the second connection sub-structure 322, and the third connection sub-structure 323.

As a result, the detection circuit 520 can respectively output electric signals to the first sub-structure 221, the second sub-structure 222, and the third sub-structure 223 and/or receive the electric signals outputted by the first sub-structure 221, the second sub-structure 222, and the third sub-structure 223. In this manner, three types of substances can be detected.

For example, addressing mode can be utilized to receive the electric signals in different sub-structures of the electrode structure, the specific implementation methods can refer to conventional design, it will not be repeated herein.

In some embodiments, as illustrated in FIG. 11, the electrochemical detection apparatus 500 can further include a working condition control unit 530. The working condition control unit 530 can be provided to control the working conditions of the electrochemical detection electrode 510.

For example, controlling the temperature, PH value or the strength of the electric field. When the electrochemical detection electrode 510 is the electrochemical detection electrode 200 as illustrated in FIG. 3A and FIG. 3B, the temperature, PH value, or strength of the electric field of the reaction solution can be changed through the working condition control unit 530.

As a result, detection grooves of different shapes can be formed under different working conditions, thus the function of detecting different substances can be respectively realized.

It should be noted, according to embodiments of the present disclosure, there are no limitations to the implementation method of the detection circuit 520, it can be implemented through general or specific circuits, digital chips or other suitable components.

There are also no limitations to the specific implementation method of the working condition control unit 530, it can be implemented through any suitable parts or components.

For example, the working condition control unit 530 can be a heating assembly, cooling assembly, PH value control assembly, electrode, and so on. For example, in some embodiments, the working condition to be controlled by the working condition control unit 530 which alters temperature.

Then, the working condition control unit 530 can include a heating component, for example, a resistance heater, heat abstractor, for example, a semiconductor cooling component, and temperature detection component, for example, a thermocouple.

In this manner, the temperature can be detected and heating or cooling can be conducted according to detection results. For example, in another embodiment, the working condition to be controlled by the working condition control unit 530 is strength of the electric field, then, the working condition control unit 530 can include a pair of electrodes facing each other, a voltage applying component, the voltage applying component can be electrically connected to the pair of electrodes, thus an electric field of preset strength can be formed between the pair of electrodes.

For example, in yet another embodiment, the working condition to be controlled by the working condition control unit 530 is PH value, then, the working condition control unit 530 can include a PH value detection electrode, an acid solution container and/or an alkaline solution container and so on. Thus the PH value of the solution can be detected and acid or alkaline can be added according to the detection results.

It should be noted, according to embodiments of the present disclosure, the electrochemical detection apparatus 500 can include less or more components, it can be determined according to the functions to be implemented, there are no limitations herein.

In another aspect of the present disclosure, a manufacturing method of an electrochemical detection electrode can be provided, the electrochemical detection electrode according to any one of the abovementioned embodiments of the present disclosure can be manufactured through this method.

The electrochemical detection electrode manufactured through this method can respectively detect a plurality of substances respectively, the detection efficiency is high, the detection sensitivity is high, uniformity is high and application range is wide.

For example, in some embodiments, the manufacturing method of the electrochemical detection electrode can include the following steps: forming an electrode structure over a substrate and forming detection grooves over the electrode structure.

In some embodiments, the electrode structure and/or detection grooves of the electrochemical detection electrode can be made through any one of any combination of the processes of microelectronic lithography, 3D/4D printing, mechanical machining, specific machining, laser process, physical self-assembly or chemical self-assembly.

In some implementations, the forming the electrode structure and the forming the detection grooves comprise forming a plurality of micron-scale detection structures with the physical self-assembly process.

In some implementations, the forming the electrode structure and the forming the detection grooves comprise forming a plurality of nano-scale structures with the microelectronic lithography process.

The nano-scale patterns or textures can also increase the surface area, and improve the detection sensitivity.

In some implementations, micron-scale detection structures can be formed utilizing a first process such as a micro-fabrication process, and then the nano-scale structures can be formed over the micron-scale detection structures utilizing a second process, such as a self-assembly process. As such, a micro-nano structure or pattern/texture can be formed.

For example, the method of physical or chemical self-assembly can include Langmuir-Blodgett membrane pulling method or templating method and so on.

In some embodiments, the electrode structure and/or detection grooves of the electrochemical detection electrode can be manufactured through Langmuir-Blodgett (LB) membrane pulling method.

Figure 13:
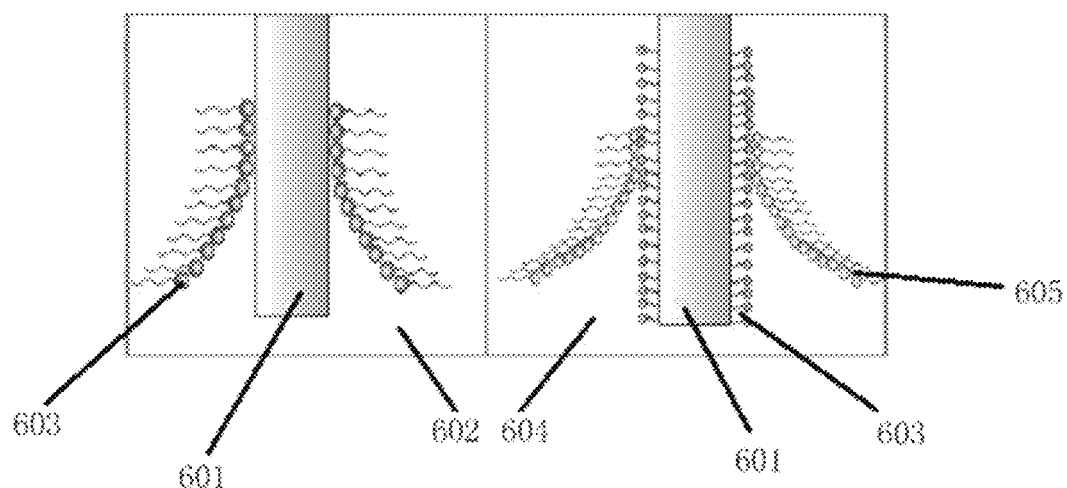
FIG. 13 is a schematic view of a self-assembly process.

As illustrated in FIG. 13, LB membrane pulling method can be utilized, the electrode substrate 601 can be immersed into the first solution 602 in the LB membrane tank, then the electrode substrate 601 can be pulled up slowly, the first monomolecular layer 603 floating over the surface of the first solution 602 can be adhered to the electrode substrate 601.

Then, the electrode substrate 601 can be immersed into the second solution 604, then the electrode substrate 601 can be pulled up slowly, the second monomolecular layer 605 floating over the surface of the second solution 604 can be adhered to the monomolecular layer 603 over the surface of the electrode substrate 601.

Through multiple times of pulling, a plurality of patterns/textures can be formed over the surface of the electrode substrate 601, then the electrode structure and detection grooves over it can be formed. For example, a plurality of patterns can be obtained through template constraint, for example, nanoscale patterns.

The pattern of the template can be manufactured through utilizing scanning tunnel microscope, or a monomolecular layer of specific nanostructure can be utilized as a template. For example, nanostructured microspheres, wherein self-assembly layer can be formed over the surface of the microspheres.

In another aspect, a method of detecting characteristics of a material with the electrochemical detection electrode described above is provided.

The method can include determining characteristics or presence of the material based on at least one of an electrical current through the electrochemical detection electrode or a resistance change of the electrochemical detection electrode.

In some embodiments, the method can further include determining a quantity of the material based on an amplitude of the electrical current or the resistance change.

It should be noted that, detailed description of the manufacturing method and technical effects of the electrochemical detection electrode according to embodiments of the present disclosure can refer to the corresponding description of the electrochemical electrode 100/200/300/400 in any of the abovementioned embodiments according to embodiments of the present disclosure.

The foregoing has provided a detailed description on an electrochemical detection electrode and manufacturing method thereof and an electrochemical detection apparatus according to some embodiments of the present disclosure. Specific examples are used herein to describe the principles and implementations of some embodiments.

The various embodiments of the present disclosure contemplated herein allow for the physical detection of a number of particular structural elements of a substance, such as the groove. In order to achieve qualitative and quantitative detection of the substance, the content of the substance can be determined by measuring the magnitude of the current in accordance with the embodiments described above. As such, current detection can be utilized so as to detect substances by detecting the associated impedance of the electrode structure.

The description is only used to help understanding some of the possible methods and concepts. Meanwhile, those of ordinary skill in the art can change the specific implementation manners and the application scope according to the concepts of the present disclosure. The contents of this specification therefore should not be construed as limiting the disclosure.

In the foregoing method embodiments, for the sake of simplified descriptions, they are expressed as a series of action combinations. However, those of ordinary skill in the art will understand that the present disclosure is not limited by the particular sequence of steps as described herein.

According to some other embodiments of the present disclosure, some steps can be performed in other orders, or simultaneously, omitted, or added to other sequences, as appropriate.

In addition, those of ordinary skill in the art will also understand that the embodiments described in the specification are just some of the embodiments, and the involved actions and portions are not all exclusively required, but will be recognized by those having skill in the art whether the functions of the various embodiments are required for a specific application thereof.

Various embodiments in this specification have been described in a progressive manner, where descriptions of some embodiments focus on the differences from other embodiments, and same or similar parts among the different embodiments are sometimes described together in only one embodiment.

It should also be noted that in the present disclosure, relational terms such as first and second, etc., are only used to distinguish one entity or operation from another entity or operation, and do not necessarily require or imply these entities having such an order or sequence. It does not necessarily require or imply that any such actual relationship or order exists between these entities or operations.

Moreover, the terms "include," "including," or any other variations thereof are intended to cover a non-exclusive inclusion such that a process, method, article, or apparatus that comprises a list of elements including not only those elements but also those that are not explicitly listed, or other elements that are inherent to such processes, methods, goods, or equipment.

In the case of no more limitation, the element defined by the sentence "includes a . . . " does not exclude the existence of another identical element in the process, the method, the commodity, or the device including the element.

In the descriptions, with respect to device(s), terminal(s), etc., in some occurrences singular forms are used, and in some other occurrences plural forms are used in the descriptions of various embodiments. It should be noted, however, that the single or plural forms are not limiting but rather are for illustrative purposes. Unless it is expressly stated that a single device, or terminal, etc. is employed, or it is expressly stated that a plurality of devices, or terminals, etc. are employed, the device(s), terminal(s), etc. can be singular, or plural.

Based on various embodiments of the present disclosure, the disclosed apparatuses, devices, and methods can be implemented in other manners. For example, the abovementioned terminals devices are only of illustrative purposes, and other types of terminals and devices can employ the methods disclosed herein.

Dividing the terminal or device into different "portions," "regions" "or "components" merely reflect various logical functions according to some embodiments, and actual implementations can have other divisions of "portions," "regions," or "components" realizing similar functions as described above, or without divisions. For example, multiple portions, regions, or components can be combined or can be integrated into another system. In addition, some features can be omitted, and some steps in the methods can be skipped.

Those of ordinary skill in the art will appreciate that the portions, or components, etc. in the devices provided by various embodiments described above can be configured in the one or more devices described above. They can also be located in one or multiple devices that is (are) different from the example embodiments described above or illustrated in the accompanying drawings. For example, the circuits, portions, or components, etc. in various embodiments described above can be integrated into one module or divided into several sub-modules.

The numbering of the various embodiments described above are only for the purpose of illustration, and do not represent preference of embodiments.

Although specific embodiments have been described above in detail, the description is merely for purposes of illustration. It should be appreciated, therefore, that many aspects described above are not intended as required or essential elements unless explicitly stated otherwise.

Various modifications of, and equivalent acts corresponding to, the disclosed aspects of the exemplary embodiments, in addition to those described above, can be made by a person of ordinary skill in the art, having the benefit of the present disclosure, without departing from the spirit and scope of the disclosure defined in the following claims, the scope of which is to be accorded the broadest interpretation to encompass such modifications and equivalent structures.

The invention claimed is:

1. An electrochemical detection electrode, comprising:
a plurality of electrode structures; and
a plurality of groups of detection structures on the plurality of electrode structures;
wherein:
the plurality of groups of detection structures comprise a first group of detection structures and a second group of detection structures, each of the first group of detection structures on one of the plurality of electrode structures has a first shape in a plane parallel to a surface of one of the plurality of electrode structures and is configured to combine with a first detection object, each of the second group of detection structures on one of the plurality of electrode structures has a second shape in a plane parallel to a surface of one of the plurality of electrode structures and is configured to combine with a second detection object; and
wherein the first shape is different from the second shape.

2. The electrochemical detection electrode according to claim 1, wherein the plurality of groups of detection structures are a plurality of detection grooves integrated on the plurality of electrode structures.

3. The electrochemical detection electrode according to claim 2, wherein each of the plurality of groups of detection structures comprises a material having temperature memory.

4. The electrochemical detection electrode according to claim 2, wherein the plurality of electrode structures comprises a first group of electrode structures and a second group of electrode structures, all of the first group of detection structures are on the first group of electrode structures, all of the second group of detection structures are on the second group of electrode structures.

5. The electrochemical detection electrode according to claim 4, wherein each of the plurality of electrode structures comprises a first part and a second part, some of the first group of detection structures are on the first part, some of the second group of detection structures are on the second part.

6. The electrochemical detection electrode according to according to claim 5, wherein some of the first group of detection structures on the first part are a material of graphene film layer, some of the second group of detection structures on the second part are a material of a diamond film layer.

7. The electrochemical detection electrode according to according to claim 6, wherein each of the plurality of electrode structures further comprises a third part, the plurality of groups of detection structures further comprises a third group of detection structures, some of the third group of detection structures are on the third part, and some of the third group of detection structures on the third part are a material of diamond-like carbon film layer.

8. The electrochemical detection electrode according to claim 7, further comprising a plurality of connection structures electrically connected to the plurality of electrode structures, wherein the plurality of connection structures are configured to transmit electric signals to the plurality of electrode structures and receive electric signals output by the plurality of electrode structures.

9. The electrochemical detection electrode according to claim 8, wherein the plurality of connection structures and the plurality of electrode structures are in one-to one correspondence.

10. The electrochemical detection electrode according to claim 2, wherein:
the electrode structure comprises a plurality of sub-structures;
the detection grooves are formed over the surfaces of the sub-structures;
the plurality of sub-structures are provided in a form of an array or in a form of a stack structure including three-dimensional cavities with shapes of at least one of a cube, a cuboid, or a cylinder.

11. An electrochemical detection apparatus, comprising:
the electrochemical detection electrode according to claim 1; and
multiple groups of detection carriers;
wherein the multiple groups of detection carriers are configured so as to be respectively utilized for surface adsorption of substances to be detected and combined with the plurality of groups of detection structures of different shapes of the electrochemical detection electrode during a detection process.

12. The electrochemical detection apparatus according to claim 11, further comprising a detection circuit and a working condition controller configured to control working conditions of the electrochemical detection electrode, wherein:
- the detection circuit is electrically coupled to the electrochemical detection electrode;
- the detection circuit is configured to transmit electric signals to the electrochemical detection electrode and receive electric signals output by the electrochemical detection electrode; and
- the working condition controller is configured to control at least one of temperature, PH value, or electric field strength.

13. A method of manufacturing the electrochemical detection electrode of claim 1, the method comprising:
- forming the plurality of electrode structures over a substrate; and
- forming a plurality of detection grooves integrally on the plurality of electrode structures.

14. The method of claim 13, wherein the forming the plurality of electrode structures and the forming the plurality of detection grooves comprise at least one of a microelectronic lithography process, a 3D/4D printing process, a mechanical machining process, a laser processing, a physical self-assembly process, or a chemical self-assembly process.

15. The method of claim 14, wherein the forming the plurality of electrode structures and the forming the plurality of detection grooves comprise forming a plurality of micron-scale detection structures with the physical self-assembly process, and forming a plurality of nano-scale structures with the chemical self-assembly process.

16. A method of detecting characteristics of a material with the electrochemical detection electrode of claim 1, the method comprising determining characteristics or presence of the material based on at least one of an electrical current through the electrochemical detection electrode or a resistance change of the electrochemical detection electrode.

* * * * *